(12) United States Patent
Arnoldussen et al.

(10) Patent No.: US 9,592,158 B2
(45) Date of Patent: Mar. 14, 2017

(54) OPERATOR-CONTROLLED SCANNING LASER PROCEDURE DESIGNED FOR LARGE-AREA EPITHELIUM REMOVAL

(71) Applicant: AMO Development, LLC., Santa Ana, CA (US)

(72) Inventors: Mark E. Arnoldussen, San Carlos, CA (US); Jonathan Wong, Milpitas, CA (US); Benjamin A. Logan, Los Gatos, CA (US); Leander Zickler, Menlo Park, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

(21) Appl. No.: 14/558,413

(22) Filed: Dec. 2, 2014

(65) Prior Publication Data

US 2015/0088104 A1    Mar. 26, 2015

Related U.S. Application Data

(60) Division of application No. 12/121,635, filed on May 15, 2008, now Pat. No. 8,926,600, which is a
(Continued)

(51) Int. Cl.
*A61F 9/008* (2006.01)
*A61B 17/00* (2006.01)

(52) U.S. Cl.
CPC .......... *A61F 9/00814* (2013.01); *A61F 9/008* (2013.01); *A61F 9/00802* (2013.01);
(Continued)

(58) Field of Classification Search
CPC ....... A61F 9/008; A61B 3/103; A61B 3/1015; A61B 18/18; A61B 3/00; B23K 26/06
(Continued)

(56) References Cited

U.S. PATENT DOCUMENTS

| 4,665,913 A | 5/1987 | L'Esperance |
| 4,941,093 A * | 7/1990 | Marshall ............. A61F 9/00804 219/121.61 |

(Continued)

FOREIGN PATENT DOCUMENTS

| WO | 97/37622 A1 | 10/1997 |
| WO | 01/08547 A2 | 2/2001 |

OTHER PUBLICATIONS

Borsutzky, A., et al.; "Tunable UV Radiation at Short Wavelengths (188-240 nm) Generated by Sum Frequency Mixing in Lithium Borate"; Applied Physics B, 1991; vol. 52, pp. 380-384.
(Continued)

*Primary Examiner* — William Thomson
*Assistant Examiner* — Victor Shapiro
(74) *Attorney, Agent, or Firm* — Abbott Medical Optics Inc.

(57) ABSTRACT

Systems and methods for removing an epithelial layer disposed over a stromal layer in a cornea irradiate a region of the epithelial layer with a pulsed beam of ablative radiation. The ablative radiation is scanned to vary the location of the beam within the region in accordance with a pulse sequence. The pulse sequence is arranged to enhance optical feedback based on a tissue fluorescence of the epithelial layer. The penetration of the epithelial layer is detected in response to the optical feedback. The use of scanning with the pulse sequence arranged to enhance optical feedback allows large areas of the epithelium to be ablated such penetration of the epithelial layer can be detected.

7 Claims, 22 Drawing Sheets

Related U.S. Application Data continuation-in-part of application No. 11/937,760, filed on Nov. 9, 2007, now Pat. No. 7,931,644.

(60) Provisional application No. 60/865,342, filed on Nov. 10, 2006.

(52) U.S. Cl.
CPC ............ *A61B 2017/00057* (2013.01); *A61B 2017/00154* (2013.01); *A61F 9/00817* (2013.01); *A61F 2009/0088* (2013.01); *A61F 2009/00844* (2013.01); *A61F 2009/00846* (2013.01); *A61F 2009/00848* (2013.01); *A61F 2009/00872* (2013.01); *A61F 2009/00882* (2013.01); *A61F 2009/00897* (2013.01)

(58) Field of Classification Search
USPC ........................... 606/5, 10, 11, 12; 351/200
See application file for complete search history.

(56) References Cited

U.S. PATENT DOCUMENTS

| | | | |
|---|---|---|---|
| 5,144,630 A | | 9/1992 | Lin |
| 5,505,724 A | | 4/1996 | Steinert |
| 5,634,920 A | * | 6/1997 | Hohla .................... A61F 9/008 606/10 |
| 5,646,791 A | | 7/1997 | Glockler |
| 5,683,379 A | | 11/1997 | Hohla |
| 5,713,892 A | | 2/1998 | Shimmick |
| 5,742,626 A | | 4/1998 | Mead et al. |
| 5,912,775 A | | 6/1999 | Glockler |
| 6,019,755 A | | 2/2000 | Steinert |
| 6,203,539 B1 | | 3/2001 | Shimmick et al. |
| 6,210,401 B1 | | 4/2001 | Lai |
| 6,245,059 B1 | | 6/2001 | Clapham |
| 6,293,939 B1 | * | 9/2001 | Steinert .................. A61F 9/008 606/5 |
| 6,331,177 B1 | | 12/2001 | Munnerlyn et al. |
| 6,347,549 B1 | | 2/2002 | Ryan et al. |
| 6,419,671 B1 | * | 7/2002 | Lemberg ................ A61B 3/103 606/11 |
| 6,592,574 B1 | | 7/2003 | Shimmick et al. |
| 6,613,041 B1 | | 9/2003 | Schruender |
| 6,984,227 B2 | | 1/2006 | Munnerlyn et al. |
| 7,008,415 B2 | | 3/2006 | Yee et al. |
| 7,077,838 B2 | | 7/2006 | Wong |
| 7,220,255 B2 | * | 5/2007 | Lai .................... B23K 26/0624 606/12 |
| 7,931,644 B2 | | 4/2011 | Arnoldussen et al. |
| 8,216,213 B2 | | 7/2012 | Gross et al. |
| 8,926,600 B2 | | 1/2015 | Arnoldussen et al. |
| 9,295,584 B2 | | 3/2016 | Holliday et al. |
| 2003/0069566 A1 | | 4/2003 | Williams et al. |
| 2003/0176855 A1 | * | 9/2003 | Gross .................... A61F 9/008 606/5 |
| 2004/0145702 A1 | * | 7/2004 | Liang .................. A61B 3/1015 351/200 |
| 2004/0147910 A1 | | 7/2004 | Fujieda |
| 2005/0102008 A1 | | 5/2005 | Wong |

OTHER PUBLICATIONS

Collins English Dictionary—Complete and Unabridged; HarperCollins Publishers 1991, 1994, 1998, 2000, 2003—Definition of Ring.
Collins Thesaurus of the English Language—Complete and Unabridged 2nd Edition, 2002, HarperCollins Publishers 1995, 2002—Definition of Disc.
International Preliminary Report on Patentability for Application No. PCT/US2007/084341, mailed on May 12, 2009, all pages.
International Search Report and Written Opinion for Application No. PCT/US2007/084341, mailed on Mar. 10, 2008, all pages.

* cited by examiner

| pulse # | est. depth | Iris (mm) | x (mm) | y (mm) | delay (ms) |
|---|---|---|---|---|---|
| 1 | 0.056249 | 2.75 | -4.4 | 0.5 | 100 |
| 2 | 0.112499 | 2.75 | -1.8 | 4 | 50 |
| 3 | 0.168748 | 2.75 | 2.7 | 2.5 | 50 |
| 4 | 0.224997 | 2.75 | 4.2 | -1.8 | 50 |
| 5 | 0.281247 | 2.75 | 2.6 | -2.8 | 50 |
| 6 | 0.337496 | 2.75 | 0.3 | -4.5 | 50 |
| 7 | 0.393745 | 3 | 0 | 0.2 | 50 |
| 8 | 0.449994 | 3 | -4.3 | 0.9 | 50 |
| 9 | 0.506244 | 3 | -2.9 | 2.8 | 50 |
| 10 | 0.562493 | 3 | 0 | 4.4 | 50 |
| 11 | 0.618742 | 3 | 1.3 | 3.9 | 50 |
| 12 | 0.674992 | 3 | 3 | 3.1 | 50 |
| 13 | 0.731241 | 3 | 4.1 | 1.5 | 50 |
| 14 | 0.78749 | 3 | 4.4 | 0.4 | 50 |
| 15 | 0.84374 | 3 | 3.7 | -1.9 | 50 |
| 16 | 0.899989 | 3 | 2.2 | -3.8 | 50 |
| 17 | 0.956238 | 3 | -0.8 | -4.3 | 50 |
| 18 | 1.01249 | 3 | -2.9 | -3.1 | 50 |
| 19 | 1.06874 | 3 | -3.8 | -1.5 | 50 |
| 20 | 1.12499 | 3 | -4.1 | -0.1 | 50 |
| 21 | 1.18124 | 3.25 | -4.3 | 0.1 | 50 |
| 22 | 1.23748 | 3.25 | -2.7 | 2.8 | 50 |
| 23 | 1.29373 | 3.25 | -1.2 | 3.4 | 50 |
| 24 | 1.34998 | 3.25 | 2.6 | 3.3 | 50 |
| 25 | 1.40623 | 3.25 | 3.3 | 1.9 | 50 |
| 26 | 1.46248 | 3.25 | 4.3 | 0.1 | 50 |
| 27 | 1.51873 | 3.25 | 3.4 | -2.6 | 50 |
| 28 | 1.57498 | 3.25 | 2.4 | -3.4 | 50 |
| 29 | 1.63123 | 3.25 | 1.1 | -4.2 | 50 |
| 30 | 1.68748 | 3.25 | -0.4 | -4.3 | 50 |
| 31 | 1.74373 | 3.25 | -2.2 | -3.7 | 50 |
| 32 | 1.79998 | 3.25 | -3.8 | -2.1 | 50 |
| 33 | 1.85623 | 3.5 | 0.4 | -0.3 | 50 |
| 34 | 1.91248 | 3.5 | -4.1 | 0.2 | 50 |
| 35 | 1.96873 | 3.5 | -3.3 | 2.6 | 50 |
| 36 | 2.02498 | 3.5 | -1.6 | 2.9 | 50 |
| 37 | 2.08122 | 3.5 | -1.6 | 3.6 | 50 |
| 38 | 2.13747 | 3.5 | 0.9 | 4 | 50 |
| 39 | 2.19372 | 3.5 | 3.2 | 2.7 | 50 |
| 40 | 2.24997 | 3.5 | 3.7 | 2 | 50 |
| 41 | 2.30622 | 3.5 | 4.1 | -0.2 | 50 |
| 42 | 2.36247 | 3.5 | 3.2 | -2.2 | 50 |
| 43 | 2.41872 | 3.5 | 0.8 | -4 | 50 |
| 44 | 2.47497 | 3.5 | -1.7 | -3.8 | 50 |
| 45 | 2.53122 | 3.5 | -3.6 | -1.6 | 50 |
| 46 | 2.58747 | 3.5 | -3.8 | -0.1 | 50 |
| 47 | 2.64372 | 3.75 | -2.5 | 1.1 | 50 |
| 48 | 2.69997 | 3.75 | -3.6 | 1.3 | 50 |
| 49 | 2.75622 | 3.75 | -2.7 | 2.7 | 50 |
| 50 | 2.81247 | 3.75 | -1.4 | 3.8 | 50 |
| 51 | 2.86871 | 3.75 | 0.3 | 3.4 | 50 |

FIG. 9

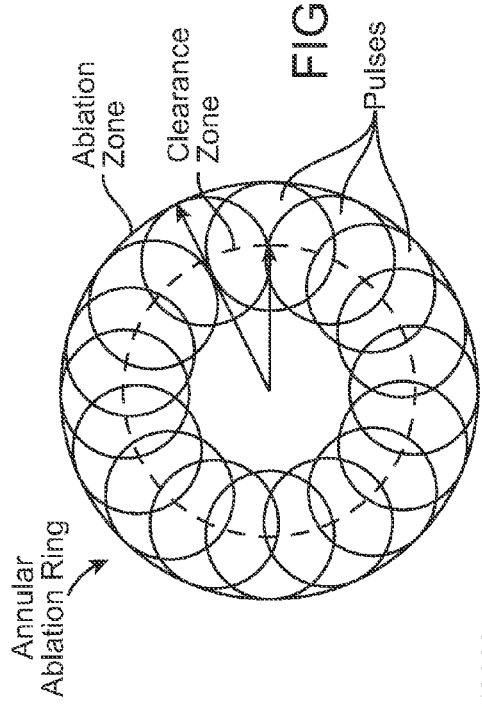
FIG. 10A1
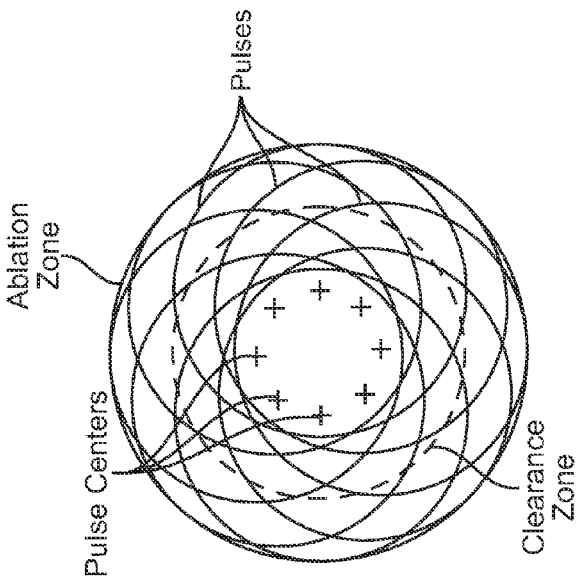
FIG. 10A3
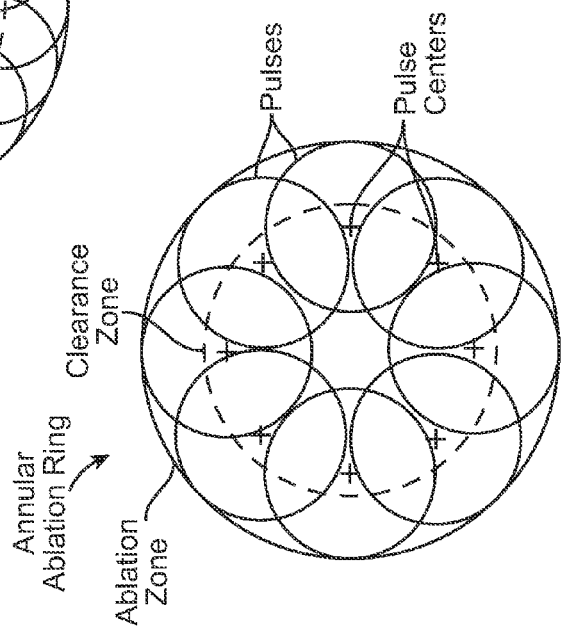
FIG. 10A2

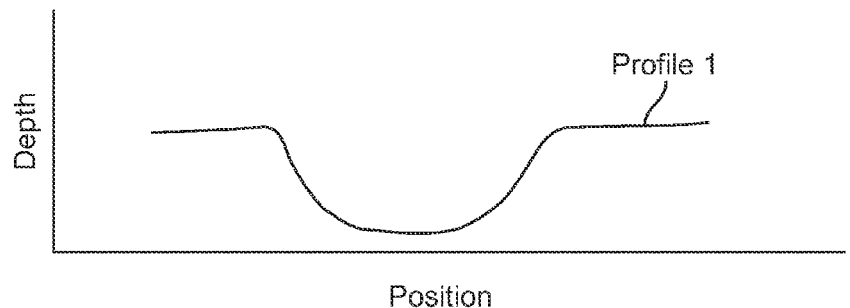
FIG. 10B1
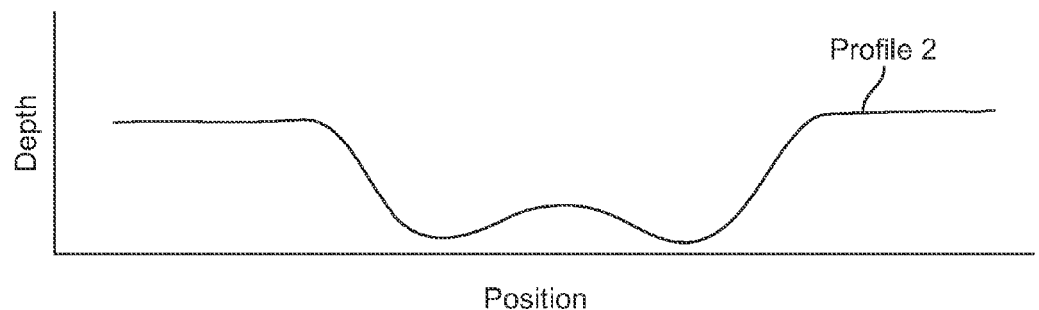
FIG. 10B2
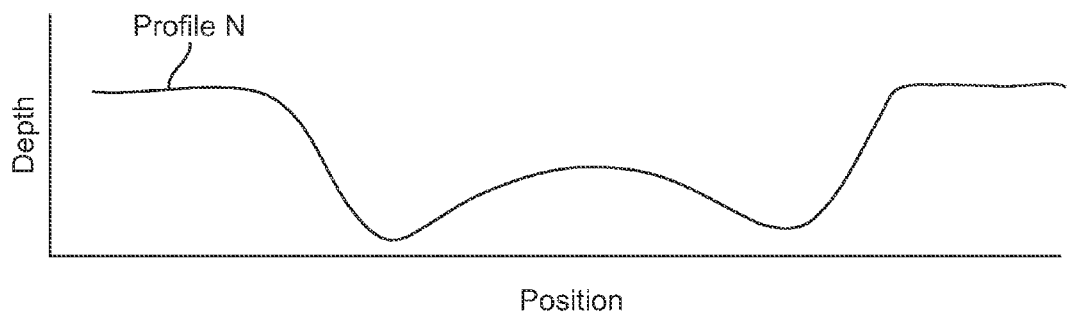
FIG. 10B3

OPERATOR-CONTROLLED SCANNING LASER PROCEDURE DESIGNED FOR LARGE-AREA EPITHELIUM REMOVAL

CROSS-REFERENCES TO RELATED APPLICATIONS

This application is a divisional and claims the benefit of U.S. application Ser. No. 12/121,635 filed May 15, 2008, which is a continuation-in-part and claims the benefit of U.S. application Ser. No. 11/937,760 filed Nov. 9, 2007, which claims the benefit under 35 USC 119(e) of U.S. Provisional Application No. 60/865,342 filed Nov. 10, 2006, entitled "OPERATOR CONTROLLED SCANNING LASER PROCEDURE DESIGNED FOR LARGE-AREA EPITHELIAL REMOVAL," the full disclosures of which are incorporated herein by reference.

BACKGROUND OF THE INVENTION

The present invention is generally related to correcting optical errors of light refracted by eyes. In exemplary embodiments, the invention provides devices, systems, and methods for correction of optical errors of eyes, and is particularly well suited for the treatment of eyes during photorefractive keratectomy (PRK) and the like.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. The lasers of these laser systems typically deliver a series of laser beam pulses during a treatment.

Known corneal correction treatment methods have generally been successful in correcting standard vision errors, such as myopia, hyperopia, astigmatism, and the like. By customizing an ablation pattern based on wavefront measurements, it may be possible to correct minor aberrations so as to reliably and repeatedly provide visual acuity greater than 20/20. Such detailed corrections will benefit from an extremely accurate ablation of tissue.

With laser ablation procedures, the epithelium is generally removed so that the permanent optical correction can be ablated into the stroma. With PRK the epithelium is removed to expose Bowman's membrane. Epithelial removal has been accomplished mechanically and with laser ablation of the epithelial layer. Mechanical removal of the epithelial layer can be accomplished with mechanical scraping of the epithelial tissue layer to expose Bowman's membrane. Another mechanical approach is to remove the epithelium with a brush. With Laser-Assisted Sub-Epithelial Keratectomy (LASEK), the epithelial layer is removed from the cornea as a sheet so that the layer can be replaced following the ablation of stromal tissue. Although these mechanical methods of epithelial removal have been successful clinically, mechanical removal of the epithelium takes time and can be perceived by the patients as invasive because the surgeon will touch the front surface of the eye with surgical instruments. Even though topical anesthesia is often applied to the cornea so that the patient cannot feel the surgeon touching his or her cornea, the patient can become nervous while the surgeon touches the front surface of the eye with the instruments, possibly delaying the procedure.

Laser ablation of the epithelium, also referred to as trans-epithelial ablation, can be less invasive and faster than mechanical approaches to removal of the epithelium. However, work in connection with the present invention suggests that the known methodologies for laser ablation of the epithelium may be less than ideal. Thus, a surgeon will often mechanically scrape the epithelium after laser removal of the epithelium to ensure that no residual epithelial debris remains before ablating stromal tissue.

In light of the above, it would be desirable to provide real-time monitoring of trans-epithelial ablations over large areas of the cornea while avoiding at least some of the limitations of known systems.

BRIEF SUMMARY OF THE INVENTION

Embodiments of the present invention provide improved devices, systems, and methods for laser treatment, for example laser treatment of eyes. More specifically, embodiments of the present invention can enhance the accuracy and efficacy of laser eye surgical procedures with improved removal of the epithelium, for example the corneal epithelium. This improved removal of the corneal epithelium can improve refractive surgical procedures, for example PRK, and can be useful for the therapeutic removal of corneal haze. While the system and methods of the present invention are described primarily in the context of a laser eye surgery system for treating the cornea of the eye, it should be understood that the techniques described herein may be adapted for use in many additional ablation procedures.

Many embodiments use a scanning laser beam that ablates an area larger than the beam and induces fluorescence of the ablated tissue layer, for example the corneal epithelium. A sequence of pulses of the beam can be arranged to enhance optical feedback based on the tissue fluorescence so that areas of the epithelium larger than the beam can be ablated and epithelial tissue penetration detected. The size and position of the pulse sequence can be arranged to overlap at least some the scanning pulses on a region smaller than the ablation, for example a central region, so that penetration of the epithelium can be detected by viewing the region. Hence, enhanced optical feedback encompasses scanning pulses with a size and position arranged to ablate an area larger than the beam and overlap the pulses on a region, or portion, of the ablated area so that penetration of the epithelium can be detected by viewing the region. In many embodiments an operator may view the region and stop the ablation in response to the enhanced optical feedback, and in some embodiments and energy detector, such as a CCD camera, may view the region ablated with a pulse sequence, for example a pulse sequence arranged to enhance optical feedback.

In a first aspect, embodiments provide a method for removing an epithelial layer disposed over a stromal layer in a cornea. A region of the epithelial layer is irradiated with a pulsed beam of ablative radiation. The ablative radiation is scanned to vary the location of the beam within the region in accordance with a pulse sequence. The pulse sequence is arranged to enhance optical feedback based on a tissue fluorescence of the epithelial layer. The penetration of the epithelial layer is detected in response to the optical feedback.

In many embodiments, the pulse sequence is sorted to enhance the optical feedback. Stromal tissue can be ablated with an optical correction in response the penetration of the epithelial layer.

In many embodiments, the epithelial layer is ablated to a first depth and an additional sub-layer of epithelial tissue is ablated to a second depth in response to the optical feedback.

In specific embodiments, the size of the laser beam is constant while the region is irradiated until the penetration of the epithelium is detected.

In another aspect, embodiments provide a method for removing an epithelial layer disposed over a stromal layer in a cornea. A region of the epithelial layer is irradiated with laser beam pulses of ablative radiation. The ablative radiation is scanned to vary the location of the beam pulses within the region. The beam is adjusted to at least one smaller beam size and at least one larger beam size while the beam is pulsed and scanned over the region in accordance with a pulse sequence arranged to enhance optical feedback. The penetration of the epithelial layer is detected based on tissue fluorescence from the larger sized beam.

In many embodiments, the irradiated region has a central region and an outer peripheral region. The adjustably sized beam can be sized and scanned so that several larger sized pulses comprise marker pulses that overlap, for example in the central region, such that the penetration of the epithelium is detected based on a decrease in fluorescence of the central region from the marker pulses.

In some embodiments, each of the marker pulses covers the central region to provide a measurement signal from the central region. In specific embodiments, the distance across the central region is about 3 mm and each marker pulse is at least about 3.5 mm across so that each marker pulse overlaps and covers the central region. The marker pulses that cover the central region may be delivered at a rate of at least about 1 Hertz to detect penetration of the epithelium.

In many embodiments, the larger beam size has a distance across of at least about 3.5 mm and the smaller beam size has a distance across of no more than about 2.5 mm. In specific embodiments, the adjustably sized beam is circular and the distance across comprises a diameter.

In many embodiments, the distance across the region is at least about 8 mm, and pulses of the larger beam size can comprise at least about 10%, for example at least about 30%, of a total number of pulses delivered before the penetration is detected.

In many embodiments, the penetration of the epithelium is detected by an operator based on the visible fluorescence of the epithelial layer irradiated with the large sized pulse.

In some embodiments, the penetration of the epithelium may be detected by an energy detector based on a fluorescence of the epithelial layer irradiated with the larger sized pulse.

In many embodiments, the adjustably sized beam is scanned and sized in accordance with a pre-programmed sequence to vary the location and size of the beam.

In many embodiments, the adjustably sized beam repeatedly changes from at least one smaller size to at least one larger size before the penetration of the epithelium is detected so that the ablated layer of epithelium is substantially uniform when the penetration of the epithelium is detected.

In many embodiments, the adjustably sized beam changes from at least one smaller size to at least one larger size at least about three times, for example five times, before the penetration of the epithelium is detected. In some embodiments, the smaller beam size is no more than about 2.5 mm across and the larger size is at least about 3.5 mm across. In specific embodiments, the smaller size may be no more than about 1.75 mm across and the larger size is at least 4 mm across.

In many embodiments, the adjustably sized beam changes from a smaller size to a larger size in correlation with an intended sub-layer of epithelial tissue ablated. In some embodiments, the intended sub-layer corresponds to an upper portion of the epithelial layer, and the adjustably sized beam changes from the smaller size to the larger size for each additional sub-layer ablated with the adjustably sized laser beam. In specific embodiments, a plurality of the additional sub-layers is ablated before the penetration of the epithelium is detected.

In many embodiments, the tissue fluorescence comprises auto-fluorescence of the tissue that originates from excitation of the molecules of the tissue with the adjustably sized laser beam.

In many embodiments, the adjustably sized beam is sized to provide at least one intermediate beam size having a cross sectional size between the at least the smaller beam size and the larger beam size.

In many embodiments, the adjustably sized beam is repeatedly sized so that the larger size comprises several beam sizes and the smaller size comprises several small beam sizes.

In another aspect, embodiments of the current invention provide a system to ablate an eye to remove an epithelial layer of the eye. A laser generates a beam of an ablative radiation. A movable scan component scans the laser beam over a region of the eye to ablate the epithelial layer. A processor system, which comprises a tangible medium and memory, is coupled to the laser and the movable scan component. The processor system is configured to scan the beam within the region in accordance with a pulse sequence arranged to enhance an optical feedback signal based on a tissue fluorescence of the epithelial layer.

In many embodiments, the processor system is configured to sort the pulse sequence to enhance the optical feedback.

In many embodiments, the system further comprises at least one lens to form an optical image of the fluorescence that is visible to an operator such that the operator can detect the penetration of the epithelial layer based on the optical feedback signal.

In another aspect, embodiments of the current invention provide a system to ablate an eye to remove an epithelial layer of the eye. The system comprises a laser to generate a beam of ablative radiation. A movable structure is disposed along the laser beam path to adjust a size of the laser beam to at least one smaller size and at least one larger size. A movable scan component is configured to scan the laser beam over a region of the eye to ablate the epithelial layer. A processor, which includes tangible medium and memory, is coupled to the laser, the movable structure, and the movable scan component. The processor is configured to ablate an epithelium with at one larger beam size and at least one smaller beam size so that a penetration of the epithelium can be detected based on a tissue fluorescence from the larger size of the beam during a procedure.

In many embodiments, the system comprises at least one of a display or a microscope to provide an image of the tissue fluorescence to an operator so that the operator can detect the penetration of the epithelium.

In some embodiments, the system may include an energy detector to detect the penetration of the epithelium based on the fluorescence.

In many embodiments, the region of the eye comprises a central region and an outer peripheral region. The processor is configured to overlap several pulses of at least one larger size of the beam in the central region to penetrate the epithelium in the central region. In some embodiments, the processor is configured to deliver the pulses with at least one larger size beam to cover the central region to provide a measurement signal from the central region. In specific embodiments, the processor can be configured to deliver pulses of the larger size beam(s) that cover the central region at a rate of at least about 1 Hertz to detect penetration of the epithelium from the measurement signal.

In many embodiments, the processor is configured to scan the laser beam over the region in accordance with a pre-programmed sequence to vary the size and location of the beam. The processor may also be configured to vary between at least one smaller size and at least one larger size to ablate the epithelium at substantially uniform rate. The processor may also be configured to vary the sized beam from at least one smaller size to at least one larger size in correlation with an intended sub-layer of ablated epithelial tissue.

In many embodiments, the small sized beam comprises a substantially circular beam with a diameter no more that about 2 mm across and the large sized beam is circular with a diameter at least about 4 mm across.

In many embodiments, the tissue fluorescence comprises an auto-fluorescence of the tissue that originates from excitation of naturally occurring molecules within tissue in which the molecules are excited with the pulsed laser beam.

In many embodiments, the movable structure may comprise an iris diaphragm, a plurality of apertures formed in a non-transmissive material or a lens.

In many embodiments, the movable scan component may comprise a movable mirror, a movable lens or a movable prism.

In another aspect, embodiments of the present invention provide a method for removing an epithelial layer disposed over a stromal layer in a cornea. A region of the epithelial layer is irradiated with a pulsed beam of an ablative radiation. The ablative radiation is scanned to vary a location of the beam within the region in accordance with a pulse sequence. The pulse sequence is arranged in response to a plurality of ring shaped basis profiles.

In many embodiments, the ablative radiation is scanned in response to a linear combination of the plurality of ring shaped basis profiles.

In many embodiments, a first of the plurality of ring shaped basis profiles is determined from a first pulse size scanned along a first circle, and a second of the plurality of ring shaped basis profiles is determined from a second pulse size scanned along a second circle. The first circle and the second circle can be sized to align an outer boundary of the first ring shaped basis profile with an outer boundary of the second ring shaped basis profile. The first pulse size and the second pulse size can be sized to align the outer boundary of the first ring shaped basis profile with the outer boundary of the second ring shaped basis profile.

In many embodiments, the pulse sequence is arranged in response to at least one disc shaped basis profile in combination with the plurality of ring shaped basis profiles. The plurality of ring shaped basis profiles may each comprise a central portion corresponding to no ablation, and the at least one disc shaped basis profile may comprise a central portion corresponding to a maximum depth of ablation of the at least one disc shape basis profile.

In another aspect, embodiments of the present invention provide a system to ablate an eye to remove an epithelial layer of the eye. The system comprises a laser to generate a beam of an ablative radiation. A movable structure is disposed along the laser beam path to adjust a size of the laser beam to at least one smaller size and at least one larger size. A movable scan component is configured to scan the adjustably sized laser beam over a region of the eye to ablate the epithelial layer. A processor system comprises a tangible medium and a memory, and the processor system can be coupled to the laser, the movable structure and the movable scan component. The processor system can be configured to scan the ablative radiation to vary a location of the beam in accordance with a pulse sequence. The pulse sequence is arranged in response to a plurality of ring shaped basis profiles.

In many embodiments, the processor system is configured to scan the ablative radiation in response to a linear combination of the plurality of ring shaped basis profiles.

In many embodiments, the processor system is configured to determine a first of the plurality of ring shaped basis profiles from a first pulse size scanned along a first circle, and the processor system is configured to determine a second of the plurality of ring shaped basis profiles is determined from a second pulse size scanned along a second circle. The processor system can be configured to size the first circle and the second circle to align an outer boundary of the first ring shaped basis profile with an outer boundary of the second ring shaped basis profile. The processor system can be configured to size the first pulse size and the second pulse size to align the outer boundary of the first ring shaped basis profile with the outer boundary of the second ring shaped basis profile.

In many embodiments, the processor system is configured to arrange the pulse sequence in response to at least one disc shaped basis profile in combination with the plurality of ring shaped basis profiles. The processor system can be configured to store the plurality of ring shaped basis profiles and each may comprise a central portion corresponding to no ablation. The processor system can be configured to store the at least one disc shaped basis profile, and the disc shaped basis profile may comprise a central portion corresponding to a maximum depth of ablation of the at least one disc shape basis profile.

In another aspect, embodiments of the present invention provide a system to ablate an eye to remove an epithelial layer of the eye. The system comprises a laser to generate a beam of an ablative radiation. A movable scan component is configured to scan the laser beam over a region of the eye to ablate the epithelial layer. A sensor is configured to measure fluorescent light and generate a signal when the beam of ablative radiation irradiates the eye. A processor system comprises a tangible medium and a memory, and the processor system is coupled to the laser, the movable scan component and the sensor. The processor system is configured to scan the beam of ablative radiation in response to the signal.

In many embodiments, the sensor is configured to detect a first portion of the region and a second portion of the region, in which the first portion comprises epithelium and the second portion comprises an exposed Bowman's membrane. The processor system is configured to direct the ablative laser beam toward the first portion and away from the portion.

In many embodiments, the sensor comprises an area configured to detect the first region and the second region. The processor can be configured to sample data from a part of the area in response to at least one of a position of the eye, a position of the beam or a size of the beam. The area may comprise pixels and the part of the area may comprises a grid comprising at least some of the pixels.

In many embodiments, the processor system is configured to detect penetration of the epithelium in response to a first amount of fluorescence and detect clearance of the epithelium in response to a second amount of fluorescence, in which the second amount is smaller than the first amount. The processor system can be configured to generate a message to an operator in response to the detection of penetration and may stop firing of the laser in response to clearance of the epithelium.

In many embodiments, the sensor is synchronized with a trigger signal to acquire an image of fluorescent light for each pulse of the beam, and the sensor is coupled to a display to display each image to an operator in real time. The sensor can be configured to acquire each image with an electronic shutter open for no more than about 1000 us, for example no more than about 100 us.

In another aspect, embodiments of the present invention provide a method ablating an eye to remove an epithelial layer of the eye. A beam of an ablative radiation is generated. The laser beam is scanned over a region of the eye to ablate the epithelial layer. A signal is generated with a fluorescent light sensor in response to the beam of ablative radiation that irradiates the eye. The beam of ablative radiation is scanned in response to the signal.

In many embodiments, the sensor detects a first portion of the region comprising epithelium and a second portion of the region comprising an exposed Bowman's membrane, and the ablative laser beam is directed toward the first portion and away from the second portion.

In many embodiments, penetration of the epithelium is detected in response to a first amount of fluorescence and clearance of the epithelium is detected in response to a second amount of fluorescence, in which the second amount is smaller than the first amount. A message to an operator can be generated in response to the detection of penetration and firing of the laser can be stopped in response to clearance of the epithelium.

BRIEF DESCRIPTION OF THE DRAWINGS

FIG. 9 shows a treatment table in accordance with an embodiment of the present invention;

FIG. 10A1 shows an ablation ring corresponding to a basis shape, in accordance with the method of FIG. 10;

FIG. 10A2 shows an ablation ring corresponding to a basis shape, in accordance with the method of FIG. 10;

FIG. 10A3 shows an ablation disc corresponding to a basis shape, in accordance with the method of FIG. 10;

FIG. 10B1 shows an ablation profile for each pulse of the ablation ring as in FIG. 10A;

FIG. 10B2 shows an ablation profile for each pulse of the ablation ring as in FIG. 10B;

FIG. 10B3 shows an ablation profile for each pulse of an ablation ring as in FIG. 10C;

DETAILED DESCRIPTION OF THE INVENTION

The present invention is particularly useful for enhancing the accuracy and efficacy of laser eye surgical procedures, such as photorefractive keratectomy (PRK), phototherapeutic keratectomy (PTK), and the like. Preferably, the present invention can provide enhanced optical accuracy of refractive procedures and improved patient comfort during the procedure by improving removal of the corneal epithelium. Hence, while the system and methods of the present invention are described primarily in the context of a laser eye surgery system for treating a cornea of the eye, it should be understood the techniques of the present invention may be adapted for use in alternative ablation procedures.

The techniques of the present invention can be readily adapted for use with existing laser systems. By providing a more rapid (and hence, may be less prone to error) methodology for correcting optical errors of an eye, the present invention facilitates sculpting of the cornea so that treated eyes may regularly receive a desired optical correction having improved vision with minimal discomfort to a patient.

As used herein a substantially constant power level encompasses a power level that is stable to within about 25% of an average power level.

Figure 1:
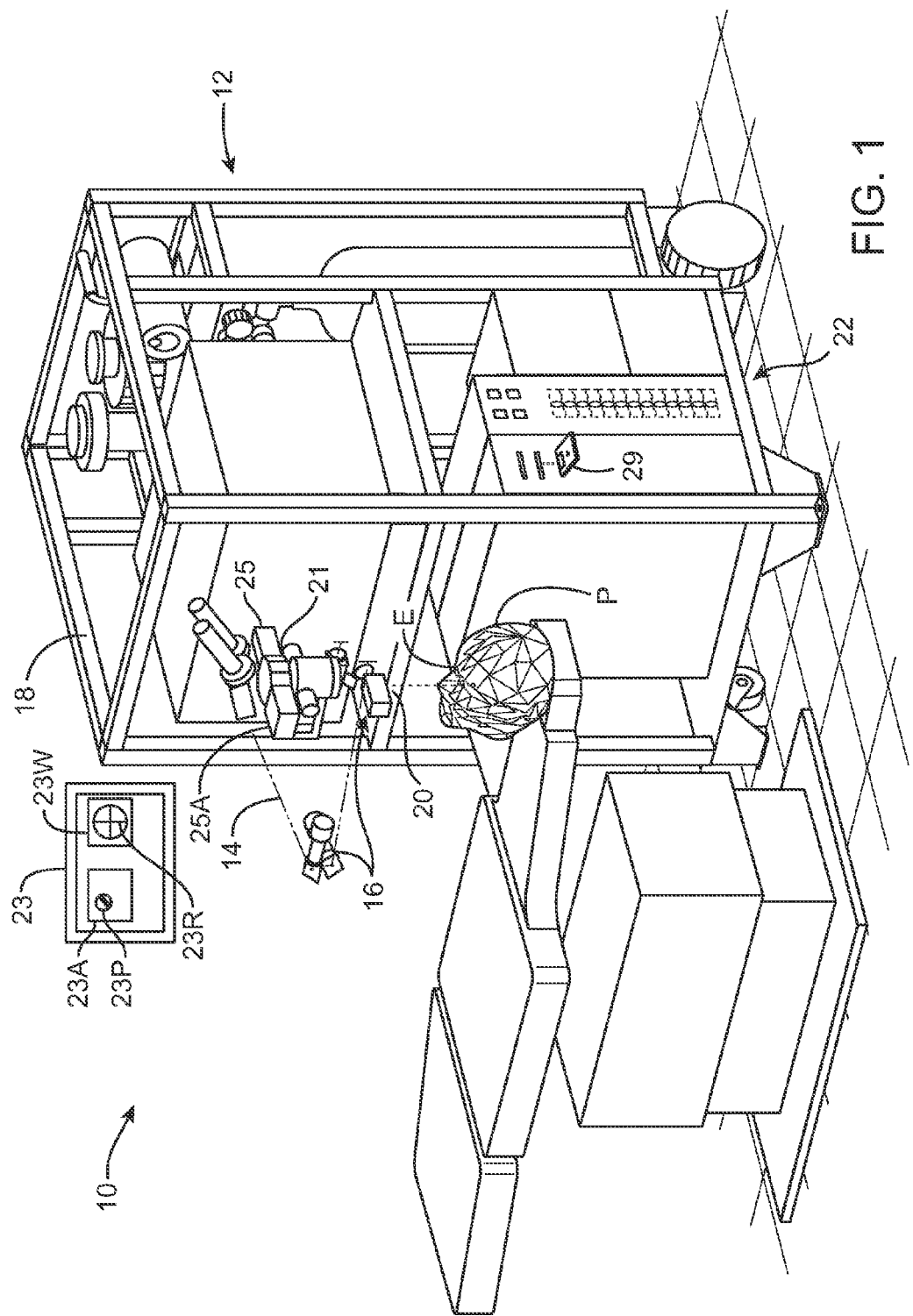
FIG. 1 is a perspective view of a laser ablation system for incorporating the invention.

Referring now to FIG. 1, a laser eye surgery system 10 for incorporating the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. An input device 20 is used to align laser system 10 with patient P. A microscope 21 is mounted on the delivery optics support structure, the microscope often being used to image a cornea of eye E. The laser eye surgery system 10 may include a display 23 that provides an image of eye E that is visible to the user. A video camera 25 can be optically coupled to microscope 21 to provide an image of the eye E on the display as seen through the microscope. Microscope 21 may comprise at least one lens to form an optical image of the tissue fluorescence that is visible to the operator such that the operator can detect penetration of the epithelial layer based on the optical feedback. In some embodiments, video camera 25 comprises a camera sensitive to visible light and at least a portion of the epithelial fluorescence comprises visible light, such that epithelial fluorescence can be seen with video camera 25. In some embodiments, a second video camera 25A can be coupled to microscope 21. Second camera 25A comprises a sensor sensitive to UV light to detect epithelial fluorescence. Second camera 25A can be triggered off the laser fire signal, such that each pulse of the treatment can be shown on the display, for example fluorescence from individual pulse 23P. Second video camera 25A may comprise an electronic shutter synchronized to the laser trigger such that the shutter is open for no more than about 1 ms, for example no more than 100 us, or even no more than 50 us, when the laser fires to enhance visibility of the epithelial fluorescence. Although a microscope is shown, in some embodiments a camera lens can be used to image the tissue fluorescence, such that the image of the tissue fluorescence can be shown on the display. In various embodiments, the laser eye surgery system 10 includes at least some portions of a Star S3 Active Trak™ Excimer Laser System and/or a STAR S4 IR™ Excimer Laser System with Variable Spot Scanning (VSS™) and WaveScan WaveFront® System available from VISX, INCORPORATED of Santa Clara, Calif.

Laser eye surgery system 10 may comprise an eye tracker 19. Eye tracker 19 may comprise, for example, an eye tracker as commercially available in the Star S3 Active Trak™ Excimer laser system and/or the STAR S4 IR™ Excimer Laser System with Variable Spot Scanning (VSS™). Eye tracker 19 may comprise optical components microscope 21. The eye tracking system may comprise at least some optical components separate from the microscope, for example as described in U.S. Pat. No. 6,322,216, the full disclosure of which is incorporated herein by reference. Eye tracker 19 can be in communication with the embedded computer so as to offset the position of the laser beam pulse in response to a measured position of the eye. The processor may comprise a processor system with at least one processor, for example a plurality of processors, such as a processor for tracking the eye, a processor to control the laser and at least one processor to control positions of scanning elements, sensors and laser firing. The processor system may comprise a distributed processor system with a first processor to calculate a treatment table, for example at a research facility, and a second processor, for example of the laser system, to ablate the eye with the treatment table from the first processor.

The display 23 may comprise windows to show images of the eye, for example a first window 23W and a second window 23A. First window 23A can be coupled to video camera 25 to show the image of the eye E as seen through the operating microscope. First window 23W may show structures visible to the operator, for example a reticule 23R, and the image of the eye including the iris and pupil. Video camera 23 may comprise a color video camera to show a color image of the eye to the operator on the display. Second window 23A can be coupled to second video camera 25A. The second video camera 25A can be coupled to a frame grabber of the embedded processor to grab an image for each pulse of the laser treatment and display the image from each pulse in window 23A of the display, so as to minimized dropped frames and facilitate detection of penetration through the epithelium. The camera synchronized to the laser beam pulse can improve epithelial fluorescence imaging and may be used for detection of penetration where the display is shown to an operator and/or where the laser pulse firing is stopped automatically. Although reference is made to a video camera, the fluorescence sensor can comprise many known sensors sensitive to fluorescence such as at least one of an area sensor, a line sensor, a CCD array, a gated image intensifier, photomultiplier tube, a photodiode, a phototransistor or a cascade detector.

While the input device 20 is here schematically illustrated as a joystick, it should be understood that a variety of input mechanisms may be used. Suitable input mechanisms may include trackballs, touch screens, or a wide variety of alternative pointing devices. Still further alternative input mechanisms include keypads, data transmission mechanisms such as an Ethernet, intranet, internet, a modem, or the like.

Laser 12 generally comprises an excimer laser, ideally comprising an argon-fluorine laser producing pulses of laser light having a wavelength of approximately 193 nm. The pulse of laser light typically has a fixed pulse duration having a full width half maximum (FWHM) of about 15 nano seconds during a treatment. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid-state lasers, including frequency multiplied solid-state lasers such as flash lamp and diode pumped solid-state lasers. Exemplary solid state lasers include UV solid state lasers (approximately 193-215 nm) such as those disclosed in U.S. Pat. Nos. 5,144,630 and 5,742,626; Borsuztky et al., "*Tunable UV Radiation at Short Wavelengths* (188-240 *nm*) *Generated by Sum Frequency Mixing in Lithium Borate*", *Appl. Phys.* 61:529-532 (1995), and the like. The laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 will generally direct laser beam 14 to the eye E of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible media 29 in the form of a treatment table, and the treatment table may be adjusted according to feedback input into processor 22 from an automated image analysis system (manually input into the processor by a system operator) in response to feedback data provided from an ablation monitoring system feedback system. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over a surface of the eye and controlling the number of pulses and/or dwell time at each location, as described, for example, by U.S. Pat. No. 4,665,913 (the full disclosure of which is incorporated herein by reference); using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

Processor 22 may comprise (or interface with) a conventional PC system including the standard operator interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal topography map, a measurement of refraction of the eye, and/or an ablation table.

Figure 1A:
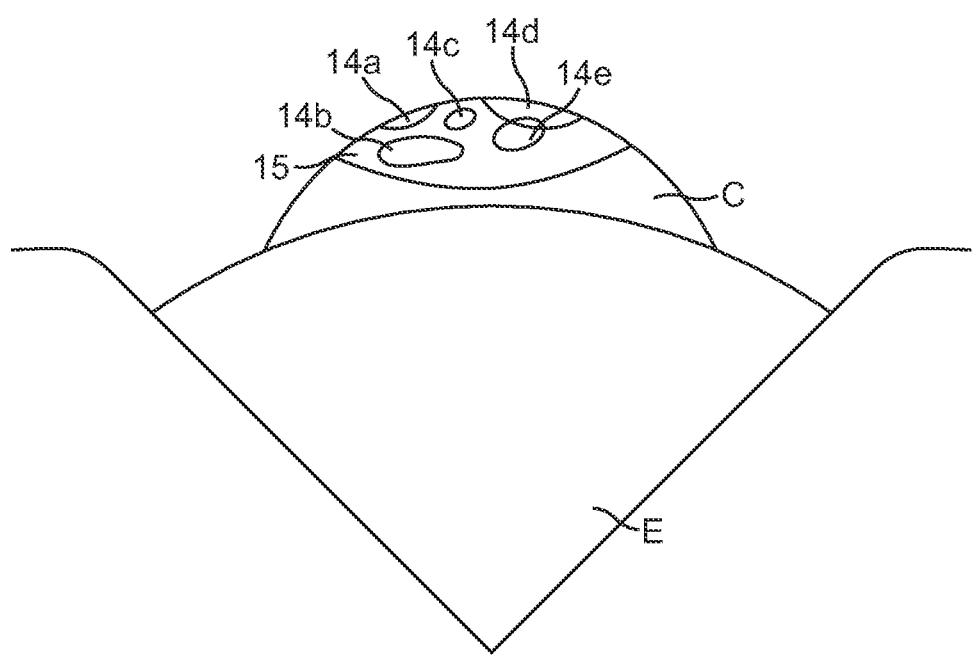
FIG. 1A illustrates an ablation of an epithelial layer of an eye using a series of scanning laser beam pulses of varying diameter applied over a region of a cornea of an eye, according to embodiments of the present invention.

An ablation of an epithelial layer eye using a series of pulses 14a-14e of a scanning laser beam is illustrated in FIG. 1A. The series of pulses are applied over a trans-epithelial ablation region 15 of a cornea C of an eye E. As illustrated in FIG. 1A pulses 14e and 14d overlap. A dimension across pulse 14c is smaller than a dimension across pulse 14b. The series of pulses 14a to 14e are sequentially applied to eye E in accordance with a treatment table listing the coordinates and sizes of the laser beam for each pulse. An additional ablation procedure can then be ablated into the stromal corneal tissue to provide a refractive correction. In some embodiments, the epithelium can be ablated to remove corneal haze.

Figure 2:
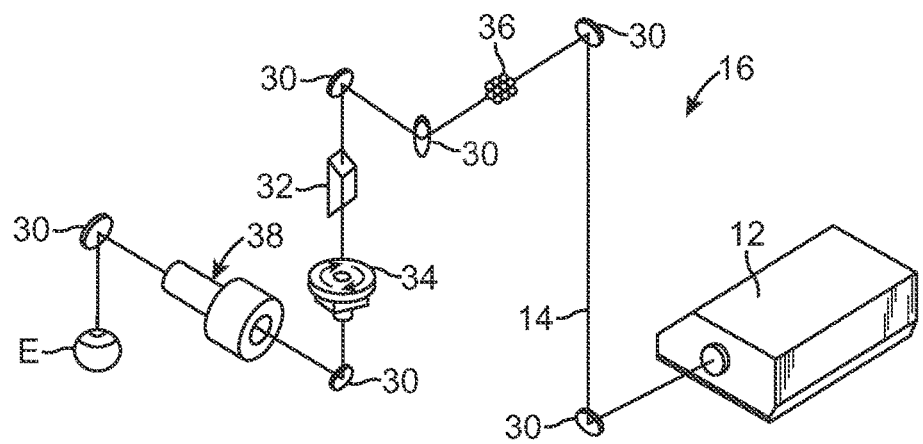
FIGS. 2 and 3 schematically illustrate a laser beam delivery system for selectively directing a laser beam onto the corneal tissue, according to embodiments of the present invention.

Referring now to FIG. 2, laser beam delivery system 16 for directing laser beam 14 at eye E will often include a number of mirrors 30, as well as one or more temporal integrators 32 which may even (or otherwise tailor) the energy distribution across the laser beam. Laser 12 will often comprise an excimer laser as described above.

Figure 3:
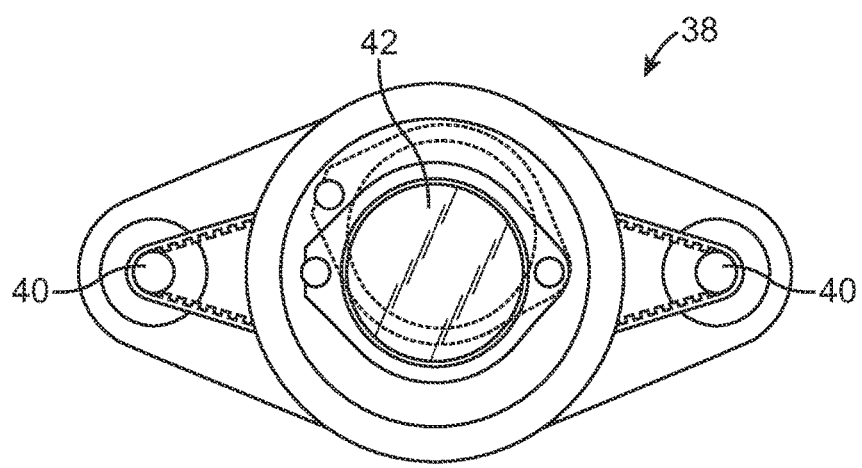

In the exemplary embodiment, a variable aperture 34 changes a diameter and/or slot width to profile laser beam 14, ideally including both a variable diameter iris and a variable width slot. A prism 36 separates laser beam 14 into a plurality of beamlets, which may partially overlap on eye E to smooth edges of the ablation or "crater" from each pulse of the laser beam. Referring now to FIGS. 2 and 3, an offset module 38 includes motors 40 which vary an angular offset of an offset lens 42, and which also change the radial orientation of the offset. Hence, offset module 38 can selectively direct laser beam 14 at a desired lateral region of the cornea. A structure and method for using laser beam delivery system 16 and offset module 38 are more fully described in U.S. Pat. Nos. 6,984,227; 6,331,177; 6,203,539; 5,912,775; and 5,646,791 the full disclosures of which are incorporated herein by reference.

Figure 4:
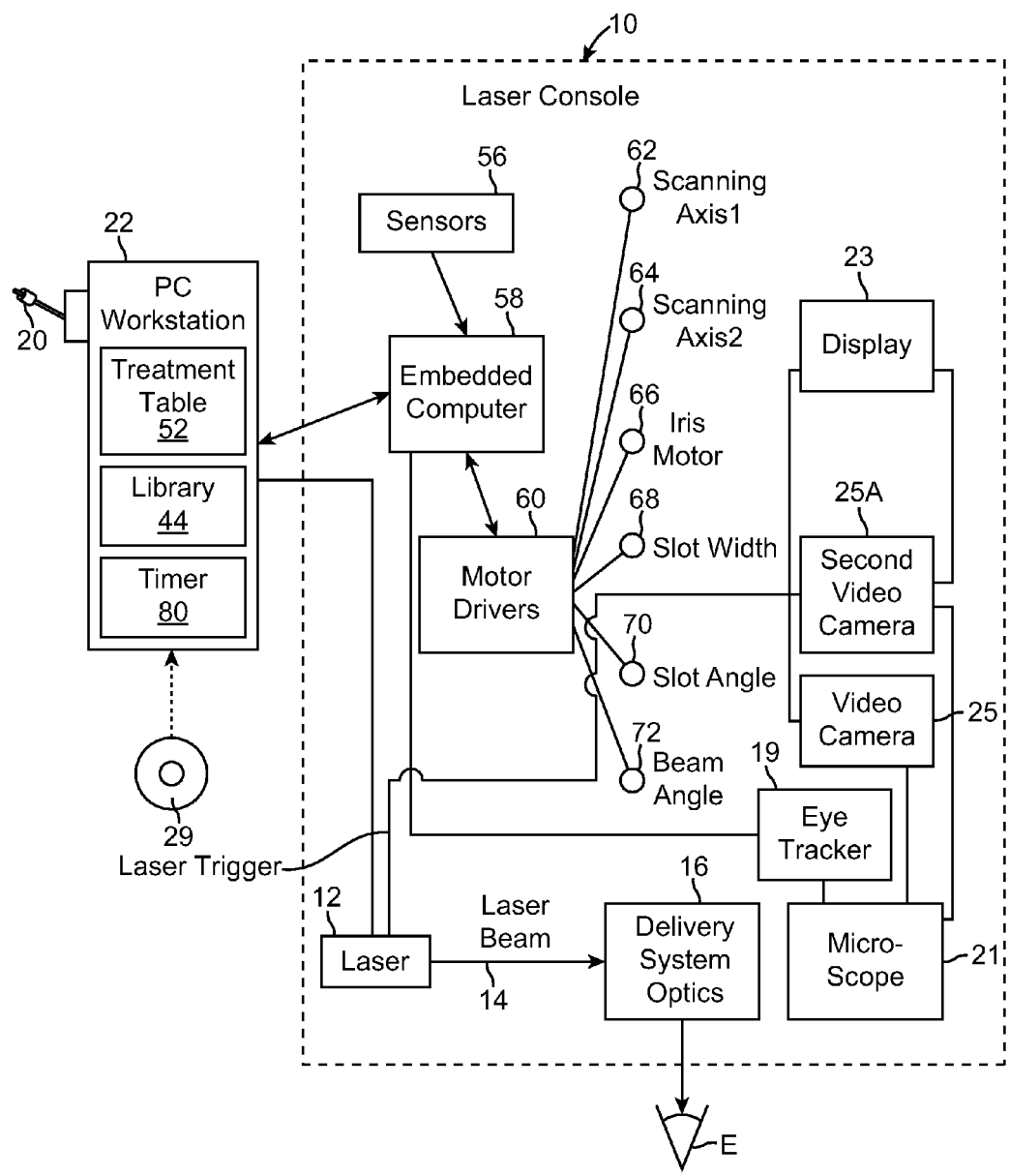
FIG. 4 is a function block diagram illustrating a control architecture of an ablation system as in FIG. 1.

Referring now to FIG. 4, a control system of a laser system 10 is schematically illustrated according to the principles of the present invention. A processor 22 enables precise control of laser system 10 to sculpt a surface shape specified in a laser treatment table 52. A processor 22, which generally comprises a PC workstation, makes use of a computer program stored on a tangible media 29 to generate treatment table 52. Processor 22 includes a library 44 of treatments and treatment tables as described in U.S. Pat. Nos. 6,245,059; and 7,077,838, the full disclosures of which are incorporated herein by reference. An embedded computer 58 within laser system 10 is in electronic communication with the PC workstation. Alternatively, a PC workstation may be embedded in the laser system and include an embedded processor card in communication with the PC workstation for directing the ophthalmic surgery. The eye tracker 19, as described above, can be connected to embedded computer 58. Video camera 25 and second video camera 25A can be optically coupled to microscope 21, as described above, and connected to display 23 to show images of the eye to the surgeon and/or system operator.

Embedded computer 58 is in electronic communication with a plurality of sensors 56 and a plurality of motor drivers 60. The motor drivers 60 are coupled to the embedded computer 58 to vary the position and configuration of many of the optical components of the delivery optics 16 according to treatment table 52. For example, first and second scanning axis 62, 64 control the position of the offset lens to move the beamlets over the surface of the cornea. Iris motor 66 controls the diameter of the overall beam, and in some cases, the length of light transmitted through a variable width slot. Similarly slot width driver 68 controls the width of the variable slot. Slot angle driver 70 controls rotation of the slot about its axis. Beam angle driver 72 controls rotation of the beam as effected by a temporal integrator as described above. Processor 22 issues a command for laser 12 to generate a pulse of the laser beam 14 after the various optical elements have been positioned to create a desired crater on eye E. Treatment table 52 comprises a listing of all of the desired craters to be combined so as to effect a treatment therapy.

A timer 80 is located on an add on card of processor 22 and is a Lab-PC-1200 model card having timers 8253/8254. The Lab-PC-1200 model card is available from National Instruments of Austin, Tex. In alternate embodiments, timer 50 is located externally to processor 22. The timer 80 is controlled by a computer program of processor 22 and is adapted to measure time intervals. The laser 12 is electronically coupled to processor 22. Laser 12 fires upon a command issued from processor 22 in response to a time interval measured by timer 80. Processor 22 varies the rate at which laser 62 fires during at least a portion of a treatment of an eye E.

Figure 5A:
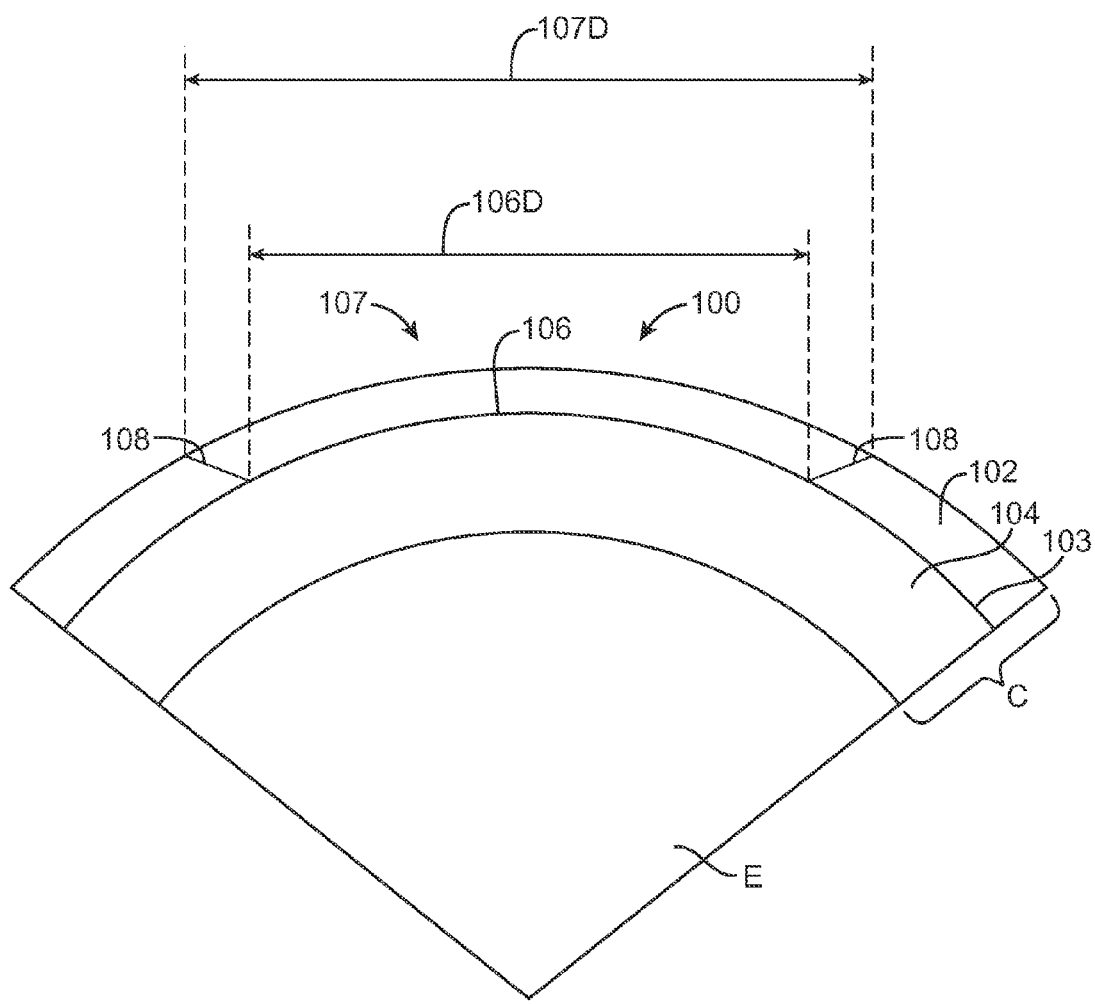
FIG. 5A shows an epithelial ablation profile of an ablated region of an epithelial layer, according to embodiments of the present invention.

FIG. 5A shows an ablation profile 107 of an ablation region 100 of an epithelial layer, according to embodiments of the present invention. Cornea C includes an epithelial layer 102 and a stromal layer 104. A Bowman's membrane 103 is disposed between epithelial layer 102 and stromal layer 104. Ablation profile 107 can include a clearance region 106 in which the epithelium is removed, and a transition zone 108 which extends from clearance region 106 to the unablated regions of the cornea. Transition zone 108 can be annular and extend with a spline, linear fit, or other connecting shape between the unablated epithelium and clearance region 106. Examples of shapes that can be used as transition zones are described in U.S. patent application Ser. No. 10/100,231, filed Mar. 14, 2002, published as US 2003/0176855, the full disclosure of which is incorporated herein by reference. Clearance region 106 can include a diameter across 106D. To optimize the ablation pulse sequence, the ablation pulse sequence can be determined with fitting of the clearance region 106 without fitting of the transition zone, which may comprise many shapes resulting from the fitting of the pulse sequence to the clearance region with the pulse instruction vector. Ablation profile 107 of ablation region 100 includes transition zone 108 and can include a diameter 107D across ablated region 107. The laser can be programmed to ablate the epithelial layer with a series of laser beam pulses in many ways, for example as described in U.S. Pat. No. 7,008,415, the full disclosure of which is incorporated herein by reference.

The characteristics of epithelial ablation profile 107 can be selected and/or adjusted by the operator as desired, and input with a treatment screen shown on a display as described above. Clearance region 107 can be selected and/or adjusted to many values, for example values from about 6.0 to about 9.5 mm. The maximum ablation zone can be about 2 mm greater than the selected clearance zone to provide an annular transition zone about 1 mm thick. In many embodiments, the width of the annular transition zone as defined from an inner circumference to an outer circumference can be selected to be from about 0.75 to 1.5 mm, although narrower sized transition zones may require addition small laser beam pulses, thereby potentially increasing treatment time. Larger sized transition zones may provide faster tissue removal with larger pulses, although in some embodiments a larger transition zone can cause the ablation to encroach on the limbus. In some embodiments, the maximum ablation width can be limited to about 12 mm. Alternatively or additionally, the maximum ablation width can be based on physiologic measurements from a wavefront machine, topography machine, or the operating microscope, such that the maximum ablation width is 1 mm less than the diameter of the limbus. The maximum depth of ablation can be about 75 microns. The thickness of the epithelial layer can be thicker peripherally than centrally such that the epithelium has a meniscus shape and the operator and/or ablation algorithm can compensate for a thicker peripheral epithelium. The thickness and optical power of the epithelium may also be related to the curvature of the cornea. The curvature of the cornea can be measured with a keratometer and/or topography machine and the keratometer values can be input by the operator and incorporated into the ablation algorithm.

Figure 5B:
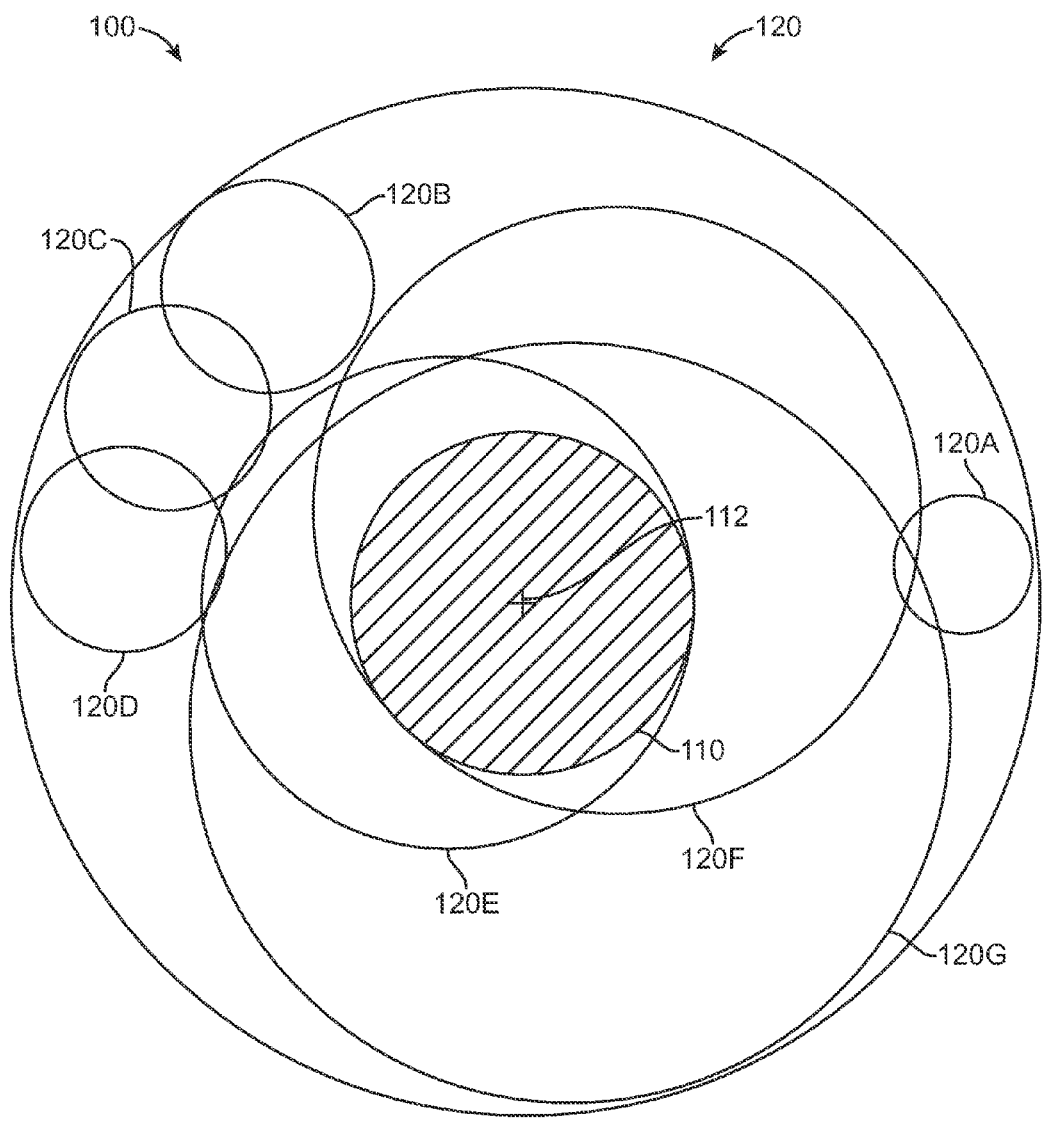
FIG. 5B shows a portion of a sequence of scanning laser beam pulses to used ablate the epithelial layer with the profile of FIG. 5A, in which the pulses are sized and positioned so as to permit detection of a penetration of the epithelial layer, according to embodiments of the present invention.

FIG. 5B shows a portion of a sequence 120 of scanning laser beam pulses to used ablate the epithelial layer with the profile of FIG. 5A, in which the pulses are sized and positioned so as to permit detection of a penetration of the epithelial layer, according to embodiments of the present invention. Although circular pulses are shown, many pulse geometries can be used, for example a variable width slit and/or variable diameter iris diaphragm, and the size of the pulse can refer to a dimension across the pulse, for example a dimension across a slit. Sequence 120 of scanning laser beam pulses can be applied to ablation region 100. Ablation region 100 can include a center 112. Sequence 120 includes individual laser beam pulses 120A to 120G. Laser beam pulses 120A to 120G are sized and positioned in ablation region 100 according to a treatment table. A cross sectional size of each of pulses 120A to 120G can refer to a cross sectional diameter of each of the pulses and position of laser beam pulses 120A to 120G can refer to a position of a center of each pulse in relation to center 112 of ablated region 100. Laser beam pulses 120A to 120D have a small cross sectional size, for example less than about 2 mm. Laser beam pulses 120E to 120G have a large cross sectional size, for example larger than about 3.5 mm. The sequence of laser beam pulses can include additional sizes of laser beam pulses, for example intermediate size pulses having a diameter greater than about 2 mm and less than about 3.5 mm. Laser beam pulses 120E to 120G overlap and cover a central region 110.

Fluorescence from central region 110 can be monitored to detect penetration of the epithelial layer. In many embodiments, the fluorescence that is monitored can comprise tissue auto-fluorescence that results from native molecules of the epithelial layer that are excited with the ablative laser radiation. In some embodiments, the fluorescence can include fluorescence that results from the excitation of a fluorescent dye applied to the epithelium, which fluoresces in response to excitation from the ablative laser radiation. Although overlap is shown in the central region, the pulse sequence can be arranged to overlap and cover other locations of the ablation region, for example peripheral regions, such that optical feedback is enhanced in the peripheral regions where the pulses overlap.

The small size laser beam pulses can include several sizes of laser beam pulses, and the large and intermediate size laser beam pulses can also include several sizes of laser beam pulses. For example, in many treatments the small sized laser beam pulses will comprises several pulses having a diameter from about 0.7 mm to about 2.5 mm, and the large size laser beam pulses will comprise several laser beam pulses having a diameter from about 3.5 to about 6.5 mm. In many embodiments, the laser beam pulses used to ablate the epithelial layer can include several intermediate sized laser beam pulses having a diameter from about 2.5 to 3.5 mm. Small size laser beam pulses can be used to provide accurate ablation of tissue and minimize residual error while medium and large pulses can provide faster tissue removal and permit the user to visualize penetration of the epithelium. In preferred embodiments, small pulses may be used initially followed by large pulses, although the pulse sequence can be sorted in many ways. In some embodiments, a laser beam pulse with a particular size can include several simultaneously generated overlapping laser beams, for example as described in U.S. Pat. No. 6,984,227, previously incorporated herein by reference.

The pulse sequence can be arranged to provide medium to large sized laser beam pulses that overlap in central region 110 to mark the penetration of the epithelium based on a decrease in fluorescence upon penetration of the epithelium. Auto-fluorescence of the epithelial layer is greater than the auto-fluorescence of the underlying stromal layer so that the pulses in central region 110 appear bright initially due to auto-fluorescence of the epithelial layer. Upon penetration into the stromal layer and many instances upon penetration into Bowman's membrane, the auto-fluorescence decreases rapidly so that penetration of the epithelium can be detected. In some embodiments, large laser beam pulses can cover central region 110 so as to permit detection of the penetration of the epithelium. Each of pulses 120E to 120G are sized with a diameter and positioned in ablated region 100 so that each of pulses 120E to 120G covers central region 110. Thus, an operator viewing the ablation of region 100 can detect penetration of the epithelium visually by observing central region 110 and monitoring the tissue fluorescence of central region 110 that results from the marker pulses applied to ablated region 100. In a preferred embodiment central region 110 has a dimension across of about 3 mm, although central region 110 can be from about 2 to 6 mm across. Also, although central region 110 is shown as circular, central region 110 can be hexagonal, triangular nor nearly any other shape that can provide a central region in which the fluorescence pattern appears substantially uniform until the epithelium is penetrated. In some embodiments, marker pulses can be applied to non-central regions of the ablation region, for example to peripheral regions, such that penetration of the epithelium can be detected peripherally with the marker pulses overlapping in the periphery of the ablated region.

The use of large to medium size pulses to mark the penetration of the epithelium can be accomplished in any number of ways. Work in relation with embodiments the present invention suggests that medium to large pulses applied to central region 110 with a frequency of at least about 0.5 Hz can provide a sufficient visual stimulus for an operator to detect penetration of the epithelial layer based on tissue auto-fluorescence in the visible portion of the spectrum of electromagnetic radiation. The marker pulses can be repeated at many frequencies from about 0.5 Hz to about 50 Hz, so that an operator can readily detect penetration of the epithelium based on the auto-fluorescence of the epithelium originating from the central region with the marker pulses. For example, in many embodiments, the marker pulses are repeated at a frequency of about 5 to 20 Hz. In preferred embodiments, about two to three marker pulses can be applied sequentially at about 20 Hz and about 1 second later an additional two to three marker pulses can be applied at about 20 Hz. Thus, the operator can readily visualize a penetrated region of the epithelium with marker pulses spaced no more than one second apart and applied with a frequency of at least about 1 Hz. In many embodiments, large central marker pulses can comprise at least about 5% of the total number of pulses used to ablate the epithelium for example from 5 to 25% of the total number of pulses delivered during ablation of the epithelium. The larger marker pulses may comprise from 5 to 50% of the total number of pulses delivered, for example 45%. In many embodiments, the large central marker pulses comprise at least about 10% of the total number of pulses used to ablate the epithelium, for example from about 10 to 15% of the total number of pulses applied to ablated the epithelium.

Figure 5C:
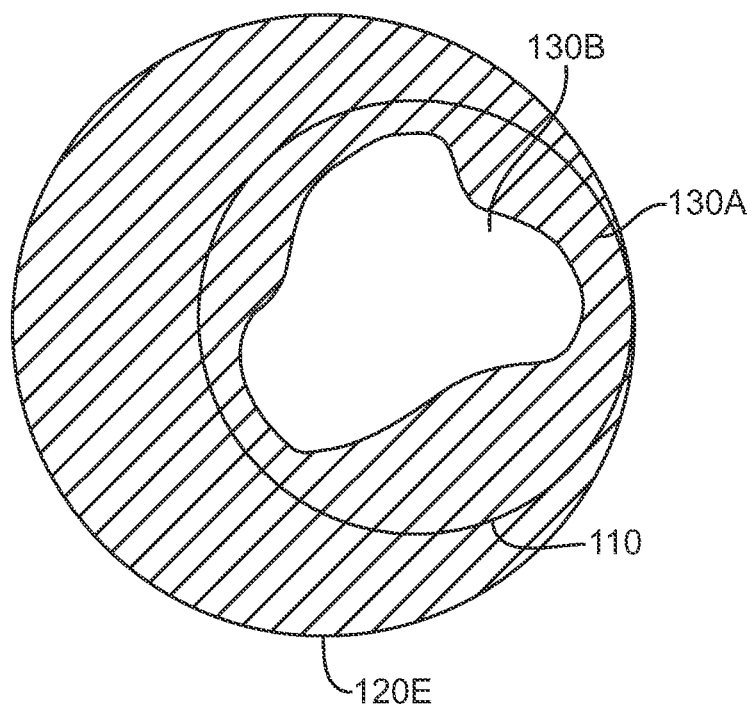
FIG. 5C shows penetration of the epithelial layer with a marker pulse of the sequence as in FIG. 5B, according to embodiments of the present invention.

FIG. 5C shows penetration of the epithelial layer with a marker pulse of the sequence as in FIG. 5B, according to embodiments of the present invention. Central region 110 is covered by pulse 120E. An epithelial fluorescence pattern 130A indicates where the epithelium has not been penetrated. A stromal and/or Bowman's fluorescence pattern 130B indicates where the epithelium has been penetrated. Subsequent pulses 120F and 120G cover central region 110 so that stromal and/or Bowman's fluorescence pattern 130B has substantially the same shape and becomes somewhat larger. Because stromal and/or Bowman's fluorescence pattern 130B has substantially the same shape with sequential pulses, stromal and/or Bowman's fluorescence pattern can be readily identified with the marker pulses to detect penetration of the epithelium. Prior to penetration of the epithelium, central region 110 has a substantially uniform fluorescence intensity which provides a substantially uniform fluorescence pattern within central region 110. Thus, an operator can readily visualize the penetration of the epithelium based on the change in tissue fluorescence within central region 110.

Figure 5D:
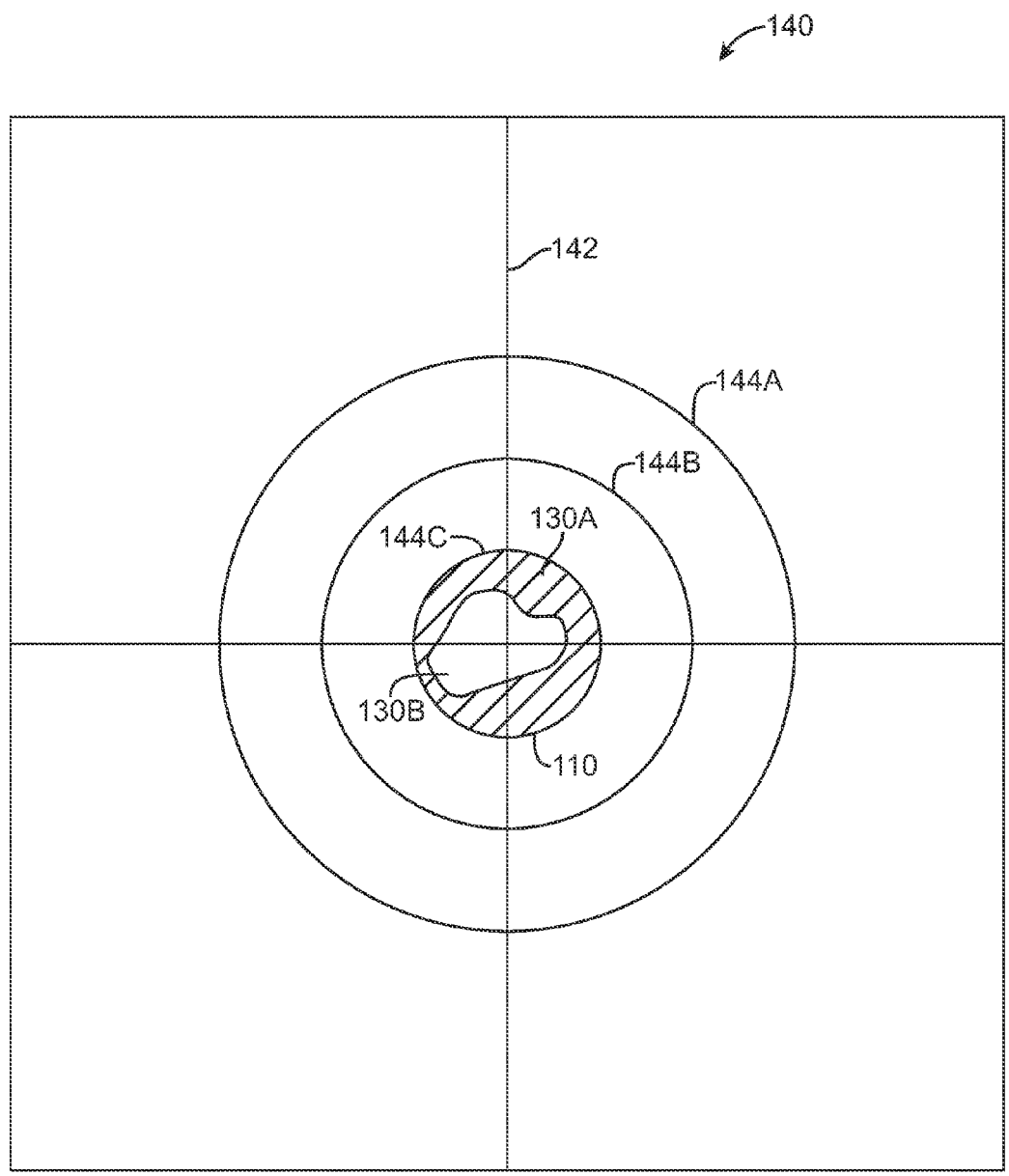
FIG. 5D shows a display visible to a system operator in which the operator can detect penetration of the epithelial layer with the pulses of FIGS. 5B and 5C, according to the embodiments of the present invention.

FIG. 5D shows an optical image 140 of the eye with a fluorescence pattern that is visible to a system operator in which the operator can detect penetration of the epithelial layer with the pulses of FIGS. 5B and 5C, according to the embodiments of the present invention. Optical image 140 can be displayed on a computer display as described above. In many embodiments, optical image 140 can be seen by the operator through an operating microscope as described above. Optical image 140 can include a reticule 142 for alignment of the ablation. Reticule 142 can include concentric circles 144A to 144C. In a preferred embodiment, reticule 144C corresponds to central region 110. The operator observes epithelial fluorescence 130A and can detect penetration of the epithelium based on the appearance of stromal and/or Bowman's ablation pattern 130B. In some embodiments, a detector, for example a CCD that detects optical image 140, can be used with the pulse sequences and optical system as described herein to automate detection of the epithelial penetration and generate an automated optical feedback control signal in response to the penetration of the epithelium. In these embodiments, the detector that detects optical image 140 has a view of eye E. The sorted pulse sequences and optical feedback as described herein can be incorporated into systems that automatically detect penetration of the epithelium to provide control signals, for example as described in U.S. Pat. Nos. 6,293,939; 6,019,755; and 5,505,724; the full disclosures of which are incorporated by reference.

The operator can respond to the visual optical feedback signal in many ways. For example, the operator can terminate the ablation of the epithelium and proceed to ablate the stroma with a desired optical and/or therapeutic correction. The ablation of the stroma can comprise an optical correction such as a wavefront ablation and/or a therapeutic ablation such as the removal of corneal haze. In many embodiments, prior to stromal ablation and after detection of epithelial penetration, the operator may respond to the detection of epithelial penetration by scraping the exposed surface to ensure that all epithelial material has been removed so that any debris that may be present does not effect the stromal ablation process.

In embodiments where epithelial penetration is not detected with a first sequence of pulses, the operator may respond to the optical feed back signal by selecting additional pulses and/or sequence(s) to ablate additional sublayers of the epithelium. In some embodiments, for example, once a first sequence of pulses corresponding to first ablation depth, for example 50 um, has been applied, the optical feedback signal may indicate that the epithelium has not been penetrated. In response, the operator may select ablation with an additional sequence of pulses corresponding to ablation of an additional layer of epithelial tissue, for example 5 um, and ablate this additional layer of tissue while observing the ablation process optical feedback provided by the sorted pulses. This process can be repeated with additional sequences that correspond to the ablation of additional layers, for example in 5 um increments, until penetration is detected in the central region or a total maximum allowed ablation depth, for example 70 um, has been achieved. The first ablation depth corresponding to the first sequence can be from about 30 to about 60 microns, for example 50 um as described above. The additional ablation depth(s) corresponding to the additional sequence(s) can correspond to depths for each layer within a range from about 1 to about 10 microns, for example 5 um as described above. The above pulses sequences can be sorted to enhance optical feedback as described above.

Again referring FIGS. 5C and 5D image processing software can be used to identify and track the epithelial breakthrough spot and then direct follow on pulses to the outer area so as to expand the breakthrough spot without ablating the identified location where the epithelium has been penetrated. An annular wide beam, for example a half-annulus, and or annular scan patter can be used to keep firing on the non-breakthrough areas and continue giving optical feedback without hitting the exposed central area where the epithelium is penetrated.

Figure 6A:
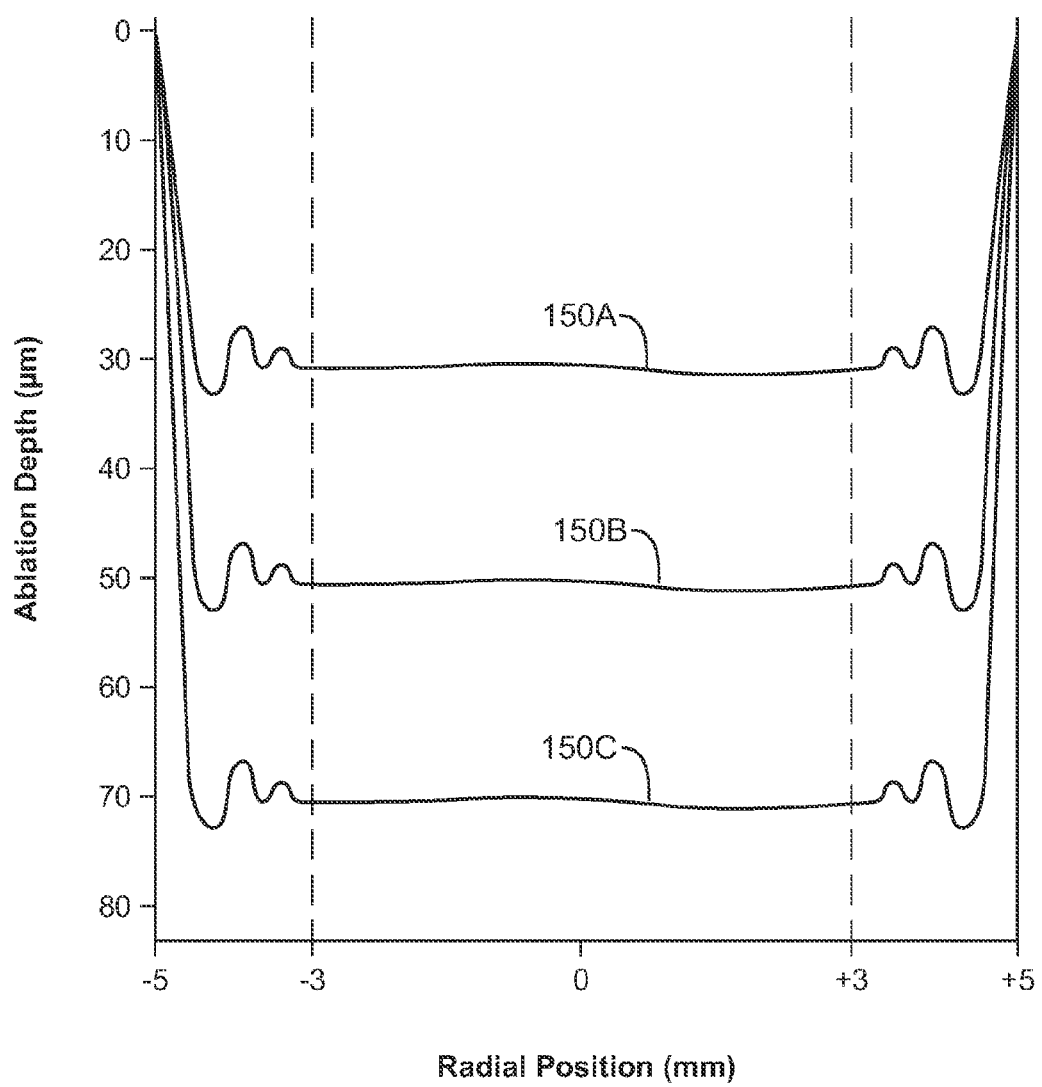
FIG. 6A illustrates theoretical ablation profiles that can be attained upon penetration of the epithelium, according to embodiments of the present invention.

FIG. 6A illustrates ablation profiles that can be attained upon penetration of the epithelium, according to embodiments of the present invention. Upon detection of penetration of the epithelium, the operator can stop the laser ablation of the epithelial surface. Thus, it is desirable that the ablated layer of epithelial tissue is smooth when the operator terminates the ablation of the epithelial surface. Ablation profile 150A shows a theoretical ablation profile that results from the operator stopping the epithelial ablation when the epithelium is penetrated at an average ablation depth of 30 microns. Ablation profile 150B and ablation profile 150C show theoretical ablation profiles for epithelial ablations terminated at average ablation depths of 50 microns and 70 microns respectively. Similar ablation profiles can be achieved for ablations terminated at many depths between 30 and 70 microns.

The ablation algorithm can be designed to provide a sequence of pulses which provide a desired amount of smoothness, based on the purpose of the underlying stromal ablation. Ablation profiles 150A to 150C show a smooth central region that extends about 6 mm across from a radial position of about −3 mm to a radial position of about +3 mm. The smooth central region corresponds to the ablated optical zone in which stromal tissue is ablated with a refractive optical correction. The smoothness of the ablated epithelial shape can have an RMS value of about 3 um or less, for example 2 um, and a peak to valley roughness of about 10 um or less, 5 um or less. The rougher peripheral region corresponds to the ablated transition zone as described above. As the transition zone is ablated may not be used to provide optical correction of stromal tissue, the exactness of the epithelial ablation over the transition zone may be less critical. In some embodiments, the roughness of the ablated transition zone can have a peak to valley roughness of 20 um or less, for example 10 um or less. As the operator may interrupt the ablation at any time, the smoothness of an ablation that is interrupted in response to penetration of the epithelium may be slightly rougher. To minimize the roughness of ablations that are terminated upon penetration of the epithelium, the pulses are arranged accordingly to provide a smooth ablation upon termination. Work in relation with embodiments of the present invention indicates that ablations terminated in response to detection of epithelial penetration can provide smooth surfaces, for example ablation surface having roughness metrics approximately twice those described for ablation to a predetermined depth.

Figure 6B:
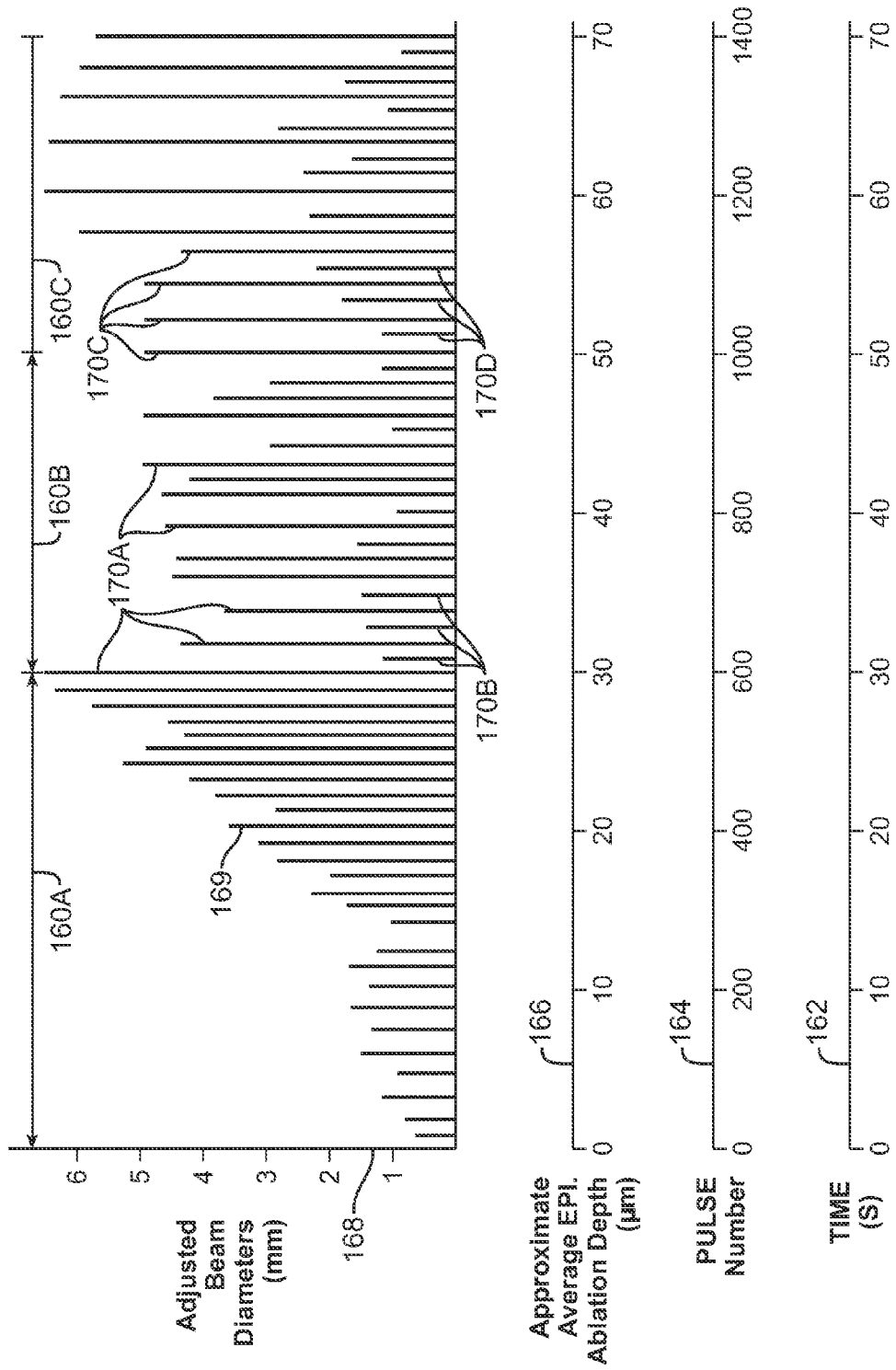
FIG. 6B shows a timing diagram illustrating pulse count, approximate average ablation depth and adjusted laser beam diameter while the laser beam pulses ablate tissue with profiles as in FIG. 6A, according to embodiments of the present invention.

FIG. 6B shows a timing diagram illustrating pulse count, approximate average ablation depth and adjusted laser beam diameter while the laser beam pulses ablate tissue with profiles as in FIG. 6A, according to embodiments of the present invention. The timing diagram includes a treatment time 162 in seconds, a pulse number 164, an approximate average ablation depth 166, and an adjusted beam diameter 168 used to ablate epithelial tissue.

For a laser with a nearly constant laser pulse firing rate, for example 20 Hz, pulse number 164 is closely correlated with treatment time 162. Although pulse number 164 increases linearly with time, in many embodiments it may be desirable to very the laser pulse firing rate by controlling a time delay between each pulse. The average depth of ablation is related to the treatment time and increases with increasing treatment time. In general, the average depth of ablation proceeds at a rate of about 1 micron per second, although slower rates can be clinically effective and acceptable.

A vertical line 169 shows adjusted beam diameter 168 for several pulses. As will be appreciated with reference to pulse number 164 and vertical line 169, vertical line 169 indicates the size of the laser beam for several pulses of the laser beam, for example about 20 pulses of the laser beam from the 400th pulse to the 420th pulse of the sequence. Thus, each vertical line that corresponds to adjusted beam diameter 168 represents several laser beam pulses of the same diameter, and these laser beam pulses of the same diameter can be scanned to different locations over the ablation region in accordance with the coordinate references of the treatment table.

Adjusted laser beam diameter 168 varies during the ablation of the epithelium. Adjusted laser beam diameter 168 includes several diameters used to ablate the first 30 microns of tissue and these diameters are indicated by arrow 160A. As the epithelial tissue layer is usually no less than 30 microns thick, laser beam pulses of increasing diameter are used to ablate the first 30 microns of tissue. If the operator terminates the ablation at a depth of 30 microns ablation profile 150A will be smooth as shown above.

Adjusted laser beam diameter 168 includes several diameters used to ablate epithelial tissue from an average depth of 30 microns to an average depth of 70 microns are indicated by arrow 160B and arrow 160C. As the epithelial tissue layer can be from 30 to 70 microns thick, laser beam pulses of alternating and/or interleaved large and small sizes can be used to ablate the epithelial tissue layer from 30 microns to 70 microns. Arrow 160B shows beam sizes for ablation from a depth of 30 to 50 microns, and arrow 160C shows ablation from a depth of 50 to 70 microns. From 30 to 50 microns, large diameter marker pulses 170A are applied to detect penetration of the epithelium, and small diameter pulses 170B are applied between marker pulses 170A to ensure that the ablation profile is smooth when the operator terminates ablation of the epithelium at a depth based on the detected penetration. From 50 to 70 microns, large diameter marker pulses 170C are applied to detect penetration of the epithelium, and small diameter pulses 170D are applied between marker pulses 170C to ensure that the ablation profile is smooth when the operator terminates ablation of the epithelium at a depth based on the detected penetration. If the operator terminates the ablation at any average ablation depth from 30 microns to 70 microns, the ablation profile will be smooth as shown above. Large beam sizes are used to remove tissue rapidly and provide marker pulses as described above, and the small beam pulses are interleaved between the marker pulses to knock down any non-uniformities in the ablation pattern that develop as the ablation proceeds.

Figure 7A:
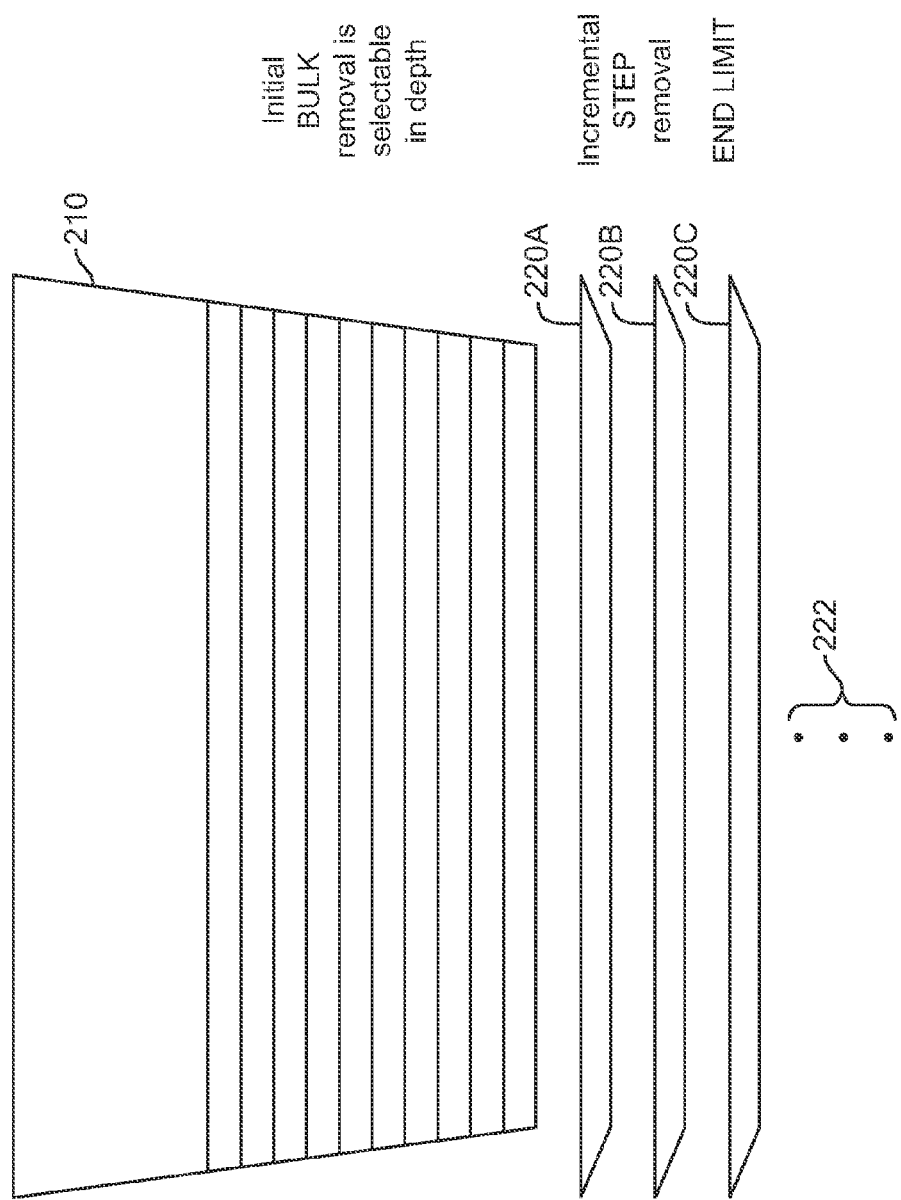
FIG. 7A shows bulk ablation of a first portion of an epithelial layer and incremental step ablation of additional sub-layers of epithelial tissue, according to embodiments of the present invention.

FIG. 7A shows bulk ablation of a first portion 210 of an epithelial layer and incremental step ablation of additional sub-layers 220A to 220C of epithelial tissue, according to embodiments of the present invention. First portion 210 of the ablated epithelial tissue can have a depth of approximately 50 microns, which corresponds to a typical thickness of the ablated epithelial layer. In some embodiments, the operator can program the bulk portion to have a selectable depth in a range from about 20 to 70 microns, for example from about 25 to 60 microns. Additional sub-layers 220A to 220C can be sequentially ablated. Additional sub-layers 222 can be ablated as needed until penetration of the epithelium is detected. Each additional sub-layer has a thickness of approximately 1 to 10 microns, for example about 5 microns. Upon completion of ablation of the bulk layer sequence, the operator can program the laser to ablate an additional sub-layer if penetration is not detected with ablation by the bulk sequence.

Figure 7B:
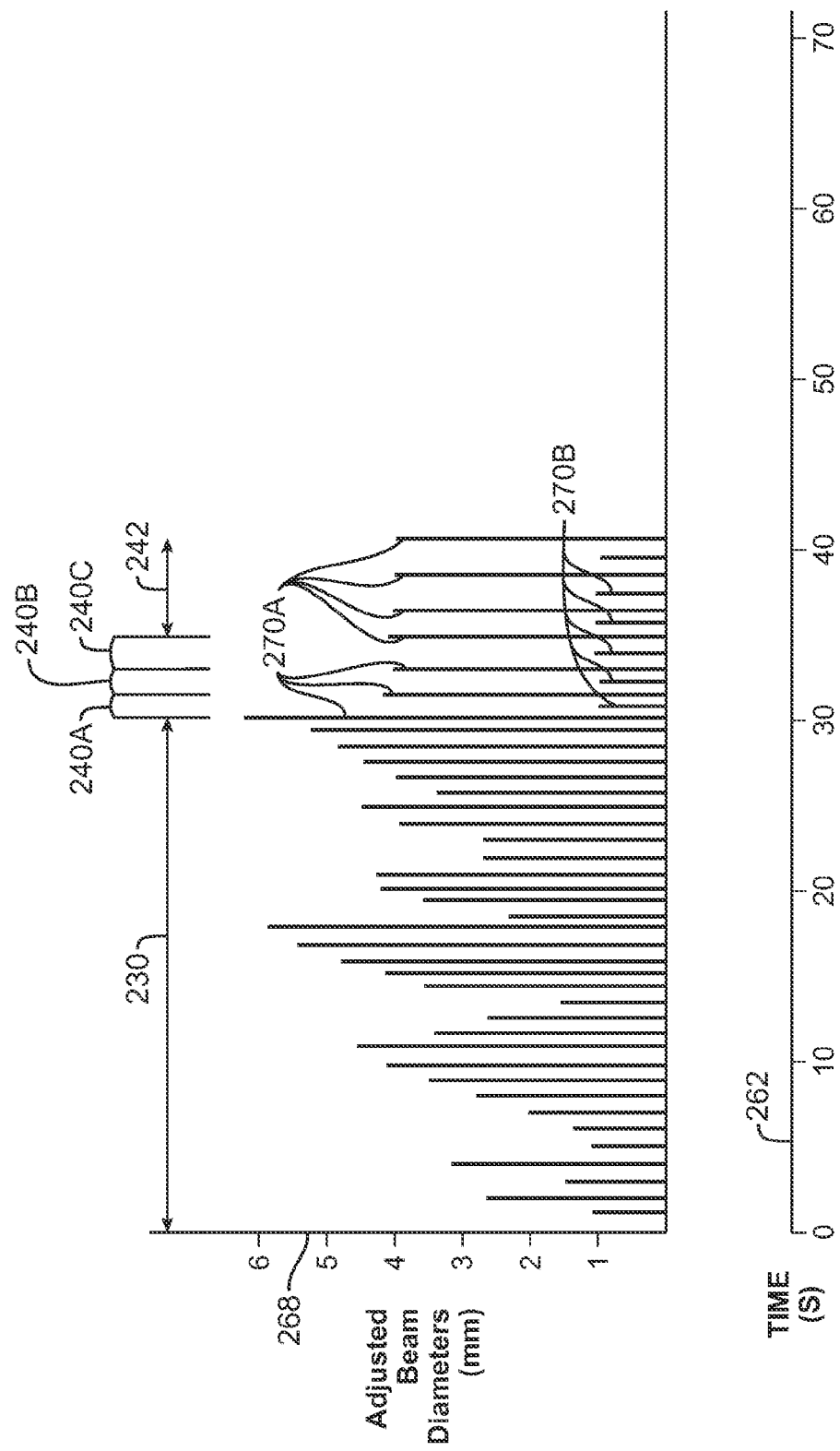
FIG. 7B shows a timing diagram illustrating approximate average ablation depth and adjusted laser beam diameter while the laser beam pulses ablate a first portion of the epithelial layer and additional sub-layers of epithelial tissue as in FIG. 7A, according to embodiments of the present invention.

FIG. 7B shows a timing diagram illustrating approximate average ablation depth and adjusted laser beam diameter while the laser beam pulses ablate a first portion of the epithelial layer and additional sub-layers of epithelial tissue as in FIG. 7A, according to embodiments of the present invention. The timing diagram includes a treatment time 262 in seconds and an adjusted beam diameter 268 used to ablate epithelial tissue. Adjusted laser beam diameter 268 varies during the ablation of the epithelium. Adjusted laser beam diameter 268 includes several diameters used to ablate first portion 210 and these diameters are indicated by arrow 230. As the epithelial tissue layer is usually no less than 30 microns thick, first portion 210 often corresponds to an ablation depth of 30 microns, and laser beam pulses of increasing diameter are used to ablate first portion 210. When the operator terminates the ablation, the ablation profile will be smooth as shown above. In some embodiments, when an operator terminates the ablation during ablation of a sub-layer of the epithelium, the laser may continue the ablation until the ablation of the sub-layer is completed so that the ablation is uniform. Thus, it may be desirable to make the sub-layers thin so that the ablation of the entire sub-layer provides an acceptably thin ablation of the underlying stromal tissue and/or Bowman's membrane.

Adjusted laser beam diameter 268 includes several diameters used to ablated sub-layers 220A to 220C. As the epithelial tissue layer can be from 30 to 70 microns thick, laser beam pulses of alternating and/or interleaved large and small sizes can be used to ablate each of the epithelial tissue sub-layers 220A to 220C. Large diameter marker pulses 270A can be applied to detect penetration of the epithelium, and small diameter pulses 270B can be applied between marker pulses 270B to ensure that the ablation profile is smooth when the operator terminates ablation based on the detected penetration of the epithelial layer. An arrow 242 indicates ablation of epithelial tissue with additional sub-layers 222 at depths below those of sub-layers 220A to 220C. Large and small pulses can be used to ablate each additional sub-layer so that the ablation is smooth when the operator terminates the epithelial ablation in response to penetration of the epithelium.

It should be noted that although FIGS. 5B to 7B make reference to embodiments in which laser beams of varying size are used to ablate the epithelium, embodiments of the present invention can employ a fixed diameter treatment beam to ablate the epithelium. Such embodiments can be readily implemented on the VISX Star™ platform by constraining the treatment table to provide a single fixed constant diameter laser beam during the ablation of the epithelial. The treatment table can be sorted to provide enhanced optical feedback in the central region of the epithelial ablation. This sorting of predetermined fixed diameter laser beam sequences can also be incorporated into laser systems such as those described in U.S. Pat. Nos. 6,635,051; 6,575,962; 6,090,110; and 5,827,264, the full disclosures of which are incorporated herein by reference. Although these embodiments that employ a constant size laser beam are within the scope and spirit of the present invention, work in relation with the present invention suggests that the variable beam embodiments described herein can provide faster ablations with improved optical feedback and improved ablation characteristics, for example smoother ablation surfaces with well defined transition zones and well defined ablation boundaries. In addition or in combination, it should be noted that solid state lasers can also be used to provide sorted ablation sequences with improved optical feedback.

Figure 8:
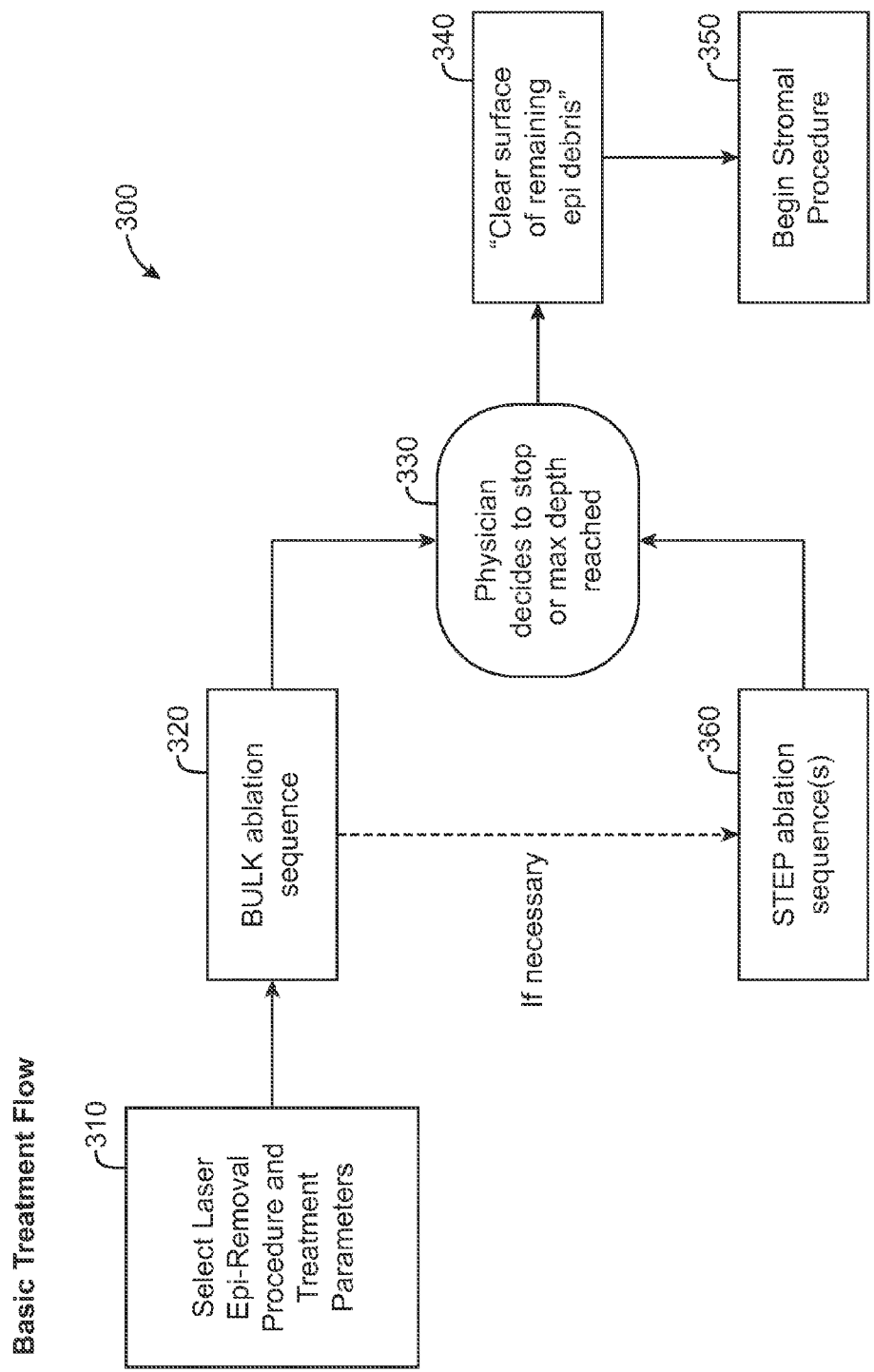
FIG. 8 shows a method of epithelial ablation, according to embodiments of the present invention.

FIG. 8 shows a method of epithelial ablation 300, according to embodiments of the present invention. A step 310 selects laser epithelial removal and treatment parameters. Example parameters include a clearance zone diameter, a total ablation diameter, and a bulk ablation depth, for example 50 microns. A step 320 applies a bulk ablation sequence of laser beam pulses. Although the bulk ablation sequence may take approximately 30 seconds, the bulk ablation treatment may take any reasonable time, for example any time from about 10 seconds to two minutes, for example about 45 seconds. A step 330 terminates and/or pauses ablation of the epithelial layer in response to detection of penetration of the epithelial layer and/or in response to completion of the bulk ablation sequence so that the epithelium has been uniformly ablated to the selected bulk ablation depth. If necessary, a step 360 selects an additional step ablation sequence, for example a sequence that ablates a 5 micron sub-layer of epithelial tissue. Step 330 terminates and/or pauses ablation of the epithelium in response to detection of penetration of the epithelial layer and/or completion of the additional sub-layer ablated. Additional step sequences can be selected with step 360 and the ablation can be terminated and/or paused at step 330 as many times as needed to detect penetration of the epithelium and/or a maximum ablation depth, for example 70 um. A step 340 may clear the surface of remaining epithelial debris, for example with mechanical scraping if desired by the treating physician. In some embodiments, the physician may not scrape the eye and use a no touch ablation procedure in which the epithelium is removed entirely with laser ablation. A step 350 begins the stromal and/or Bowman's ablation procedure, for example to correct refractive error of the eye such as wavefront aberrations.

It should be appreciated that the specific steps illustrated in FIG. 8 provide a particular method of measuring ablation according to an embodiment of the present invention. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added or removed depending on the particular applications. One of ordinary skill in the art would recognize many variations, modifications, and alternatives.

FIG. 9 shows a treatment table 900 in accordance with an embodiment of the present invention. Treatment table 900 includes several parameters to control the pulse size, location and delay for each pulse of the laser beam. A pulse number 910 indicates the pulse number of the sequence. An estimated depth 920 corresponds to the estimated average ablation depth for each pulse number. An iris diameter 930 indicates that diameter of the laser beam on the eye for each pulse of the laser beam. An x-coordinate 940 lists the x-coordinate location on the center of the sized laser beam on the eye for each pulse of the laser beam. A y-coordinate 950 lists the y-coordinate of the center of the sized laser beam on the eye for each pulse of the laser beam. A delay 960 lists the delay from the previous pulse for each pulse of the laser beam, so that the laser pulse repetition rate can be controlled for each pulse of the laser beam. For example delay 960 listed as 50 ms corresponds to a laser firing rate of 20 Hz, and delay 960 listed as 100 ms corresponds to a laser firing rate of 10 Hz. Appendix A, incorporated herein by reference, lists the entire treatment table 900 to an average ablation depth of about 63 microns for about 1100 pulses.

While the present invention has been described with respect to particular embodiments and specific examples thereof, it should be understood that other embodiments may fall within the spirit and scope of the invention. The scope of the invention should, therefore, be determined with reference to the appended claims along with their full scope of equivalents.

Figure 10:
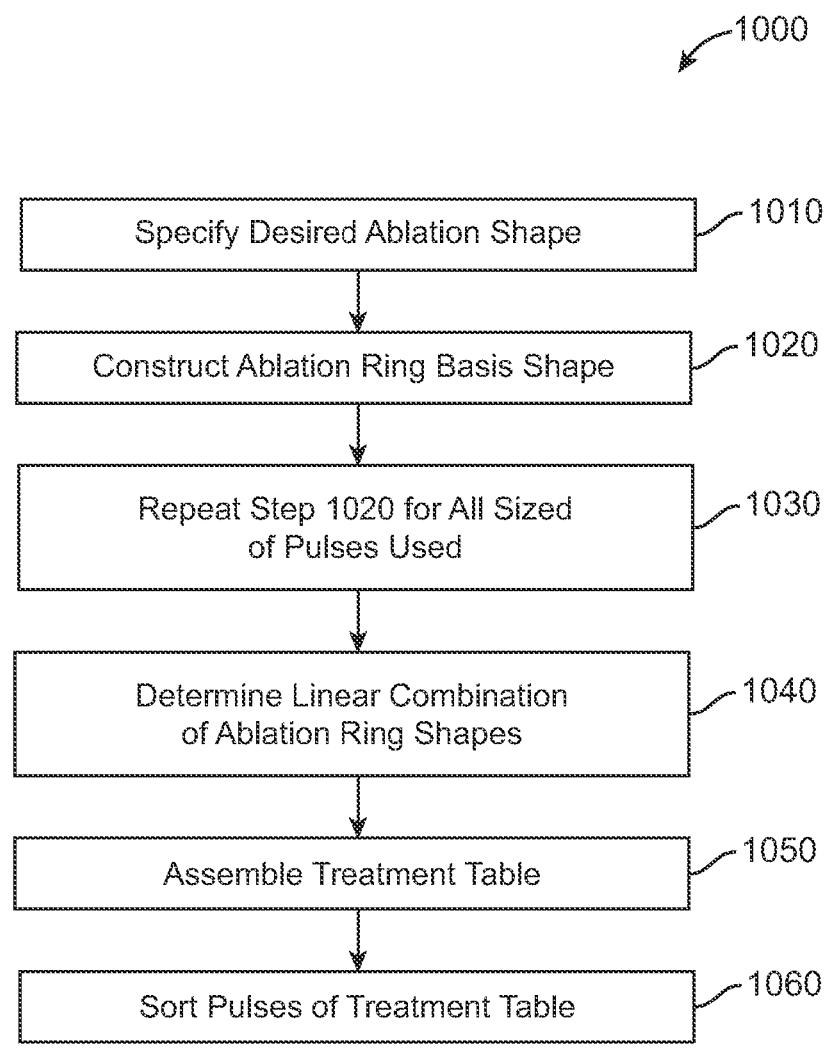
FIG. 10 shows a method of generating a laser treatment table, according to embodiments of the present invention.

FIG. 10 shows a method 1000 of generating a laser treatment table. Method 1000 may generate useful laser beam pulses, and may comprise basis shapes and/or target warping. Method 1000 can be implemented on the processor and/or controller of the laser surgery system as described above. Method 1000 may be implemented with a processor system, for example a processor system in which a first processor at a first location determines treatment tables and a second processor at a second location treats the patient with the table generated with the first processor. A sequence of pulses of the beam can be arranged to enhance optical feedback based on the tissue fluorescence so that areas of the epithelium larger than the beam can be ablated and tissue penetration detected, for example with sorting and pulse sizes as described above.

A step 1010 specifies the desired ablation shape. While the desired shape can be specified in many ways, the following ablation parameters may be used. A clearance zone can be chosen, for example a 9 mm clearance zone. The clearance zone may comprise the ablation area where it is intended for the epithelium to be removed. A maximum ablation diameter can be chosen, for a 12 mm maximum ablation diameter. The maximum ablation diameter may comprise the maximum diameter may comprise a dimension of the ablation over which tissue is ablated. The maximum ablation diameter may comprise the clearance zone and an annular ablation region, over which annular region epithelium may not be completely removed. A depth of epithelium can be chosen, for 50 microns. A mean curvature of the cornea can be entered, for example based on a keratometry curvature of 45 Diopters. The desired ablation shape may be compensated in response to the keratometery and a cosine effect of the laser ablation process, in which cosine effect the surface of the cornea normal vector deviates from a direction of propagation of the laser beam, such that the localized fluence as the ablation may be reduced by the absolute value of the cosine of the surface normal vector of the cornea with the direction of propagation of the laser beam. The target shape can be generated by incorporating desired ablation dimensions, for example ablation profiles along two dimensions, and compensating for cosine effect based on mean keratometry and/or corneal topography. A processor that determines angles between a curved surface and a laser beam is described in U.S. Pat. No. 7,083,609, the full disclosure of which is incorporated herein by reference and may be suitable for combination with embodiments of the present invention.

A step 1020 construct an ablation ring basis shape. For example, with largest diameter pulse available on a laser, for example a 6.5 mm ablation, an ablation ring basis shape is constructed. The largest size of 6.5 mm is merely an example, and the largest size can be 5.0 mm, 2.0 mm or even 1.0 mm or less. The ablation ring basis shape may comprise of the sum of 100 identically sized pulses evenly spaced along a circular path. The circular path can be concentric with the desired shape, and the pulses can be positioned such that the edge of each pulse just touches the edge of the ablation. In a specific embodiment, the pulses may lie along a circular path whose diameter is the ablation diameter minus the pulse diameter. For example, for a desired shape with an ablation diameter of 12 mm, a ring of 6.5 mm pulses would be placed in a circle with a diameter of 12 mm−6.5 mm=5.5 mm.

A step 1030 repeat step 1020 for all sizes of pulses that may be used for the ablation. For example step 1020 can be repeated with for each pulse diameter of approximately 6.0 mm, 5.5 mm, 5.0 mm, 4.5 mm, 4.0 mm, 3.5 mm, 3.0 mm, 2.5 mm, 2.0 mm, 1.5 mm, 1.0 mm and 0.5 mm. Although 0.5 mm increments are listed, the increment may comprise many values from about 0.1 to 6 mm available with the laser system, for example increments of 0.25 mm. The set of ablation ring shapes determined at each increment may comprise basis shapes.

A step 1040 determines a linear combination of ablation ring shapes to approximate the desired ablation shape, for example a weighting factor for each shape. The linear combination of these ablation ring shapes that best approximates the desired shape can be determined in many ways, for example with computerized optimization such as least squares fitting and/or simulated annealing. Generating laser scanning spot locations for laser eye surgery is described in U.S. Pat. No. 7,008,415, the full disclosure of which has been incorporated herein by reference, and the disclosure of this patent may be suitable for combination with some embodiments of the present invention. The liner combination may comprise a weighting factor for each ring, the weighting factor determined for each ring may describe the number pulses to place in that ring. The weighting factors may not be negative as ablation generally corresponds to removal of tissue. Any individual weighting factor may be greater than or equal to a threshold value, for example greater than or equal to 0.2, to provide a threshold number of pulses per rind, for example at least 20 pulses per ring. The algorithm may be biased toward using more of the larger pulses than the smaller pulses, since the lager pulses have a higher volume removal rate than smaller pulses.

A step 1050 assembles the treatment table. The table can be assembled by putting the determined number of pulses into each ring in response to the linear combination and/or weighting factor. For example, the determined number of pulses may comprise the determined weighting factor of the ring times 100 pulses, for example when the basis shape is determined with 100 pulses. The table can be sorted such that the pulses in each ring are evenly spaced along a circular path.

A step 1060 may sort the entire set of ablation pulses then sorted according to the following criteria: a) The ablation is divided into multiple passes so that it progresses uniformly and so that the large pulses, whose fluorescence is easier to see, occur regularly throughout the entire ablation process; b) The pulses are sorted to minimize pulse-to-pulse overlap; this is done to try to minimize heat build-up; c) The pulse-to-pulse delays are minimized so as to minimize the overall ablation time; this minimization may be constrained by corneal heating limits and may use the algorithm used to determined the linear combinations.

It should be appreciated that the specific steps illustrated in FIG. 10 provide a particular method of generating a laser treatment table according to an embodiment of the present invention. Other sequences of steps may also be performed according to alternative embodiments. For example, alternative embodiments of the present invention may perform the steps outlined above in a different order. Moreover, the individual steps illustrated in FIG. 10 may include multiple sub-steps that may be performed in various sequences as appropriate to the individual step. Furthermore, additional steps may be added or removed depending on the particular applications. One of ordinary skill in the art would recognize many variations, modifications, and alternatives.

FIG. 10A1 shows an annular ablation ring corresponding to a first basis shape with a first pulse size. The annular ablation ring is formed with ablation from a plurality of pulses having substantially the same diameter, for example 2.0 mm+/−0.2 mm. The plurality of pulses can be applied with a center of each pulse along a circle, for example a first circle that corresponds to the clearance zone. The pulse center circle and pulse diameter are sized such that the edge of each pulse is positioned along a circular boundary of the ablation, for example an outer circle of the annular ablation pattern. The outer boundary of the ablation may have a diameter, for example of 10 mm.

FIG. 10A2 shows an ablation ring corresponding to a second basis shape with a second pulse size. The annular ablation ring is formed with ablation from a plurality of pulses having substantially the same diameter, for example 4.0 mm+/−0.2 mm. The plurality of pulses can be applied with a center of each pulse along a circle, for example a second circle that positions the pulse centers inside the clearance zone. The pulse center circle and pulse diameter are sized such that the edge of each pulse is positioned along a circular boundary of the ablation, as in FIG. 10A1. The outer boundary of the ablation may have a diameter that matches the outer boundary of the first basis shape, for example 10 mm.

FIG. 10A3 shows an ablation disc corresponding to an Nth basis shape. The Nth basis shape shows that several basis shapes can be formed, for example annular and or discs, with increments of pulse size as described above. The ablation disc can be formed with ablation from a plurality of pulses having substantially the same diameter, for example 6.0 mm+/−0.2 mm. The plurality of pulses can be applied with a center of each pulse along an Nth circle, for example a circle that positions the pulse centers inside the clearance zone. The pulse center circle and pulse diameter can be sized such that the edge of each pulse is positioned along a circular boundary of the ablation, as in FIGS. 10A1 and 10A2. The outer boundary of the ablation may have a diameter that matches the outer boundary of the first basis shape and second basis shape, for example 10 mm.

FIG. 10B1 shows an ablation profile for each pulse of the ablation ring as in FIG. 10A. It may be desirable to determine the shape of tissue removed with each pulse of the laser beam. Profile 1 shows the shape profile of tissue removed with each pulse of the laser beam for the first pulse size, for example the 2 mm pulse size, scanned with a center of each pulse along a first circle. The shape profile of tissue removed with each pulse of the laser beam can be determined for each pulse diameter. The shape of tissue removed with each pulse can be determined based on measured ablation profiles, for example as described in U.S. Pat. No. 6,302,876, the full disclosure of which is incorporated herein by reference. The shape of tissue removed with each pulse can be summed over the ablation zone to determine the basis profile. For example the profile of the 2 mm beam can be applied to over the ablation ring to determine the shape of tissue removed with the ring, for example with 100 pulses.

FIG. 10B2 shows an ablation profile for each pulse of the ablation ring as in FIG. 10B. Profile 2 shows the shape profile of tissue removed with each pulse of the laser beam for the second pulse size, for example the 4 mm pulse size, scanned with a center of each pulse along a second circle. The shape of tissue removed with each pulse can be summed over the ablation zone to determine the second basis profile. For example the profile of the 4 mm beam can be applied to over the second ablation ring to determine the shape of tissue removed with the ring, for example with 100 pulses.

Figure 10C:
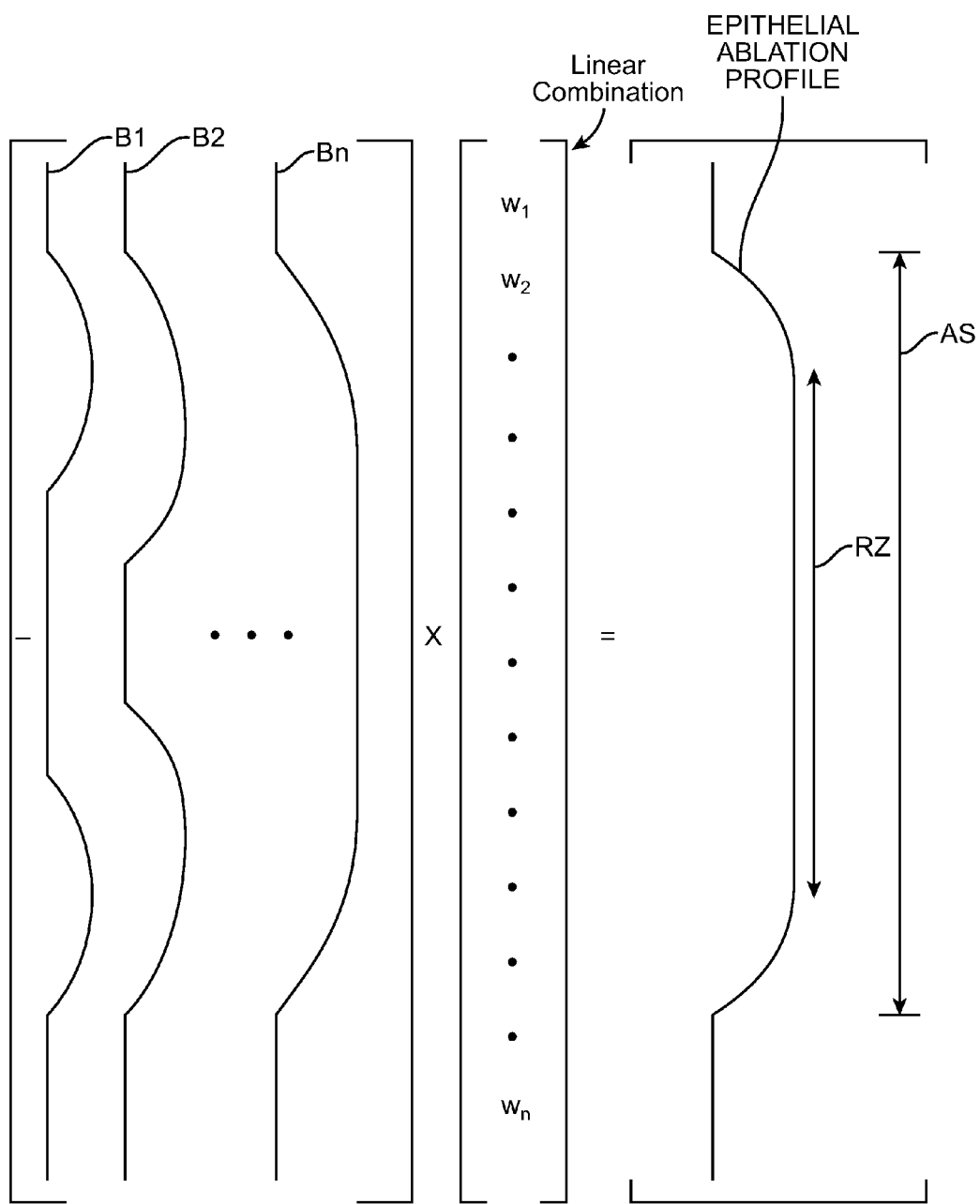
FIG. 10C shows fitting of basis profiles from the ablation rings and discs as in FIGS. 10A, 10B and 10C to determine a linear combination of basis profiles.

FIG. 10B3 shows an ablation profile for each pulse of an ablation ring as in FIG. 10C. Profile N shows the shape profile of tissue removed with each pulse of the laser beam for the Nth pulse size, for example the 6 mm pulse size, scanned with a center of each pulse along an Nth circle. The shape of tissue removed with each pulse can be summed over the ablation zone to determine the second basis profile. For example the profile of the 6 mm beam can be applied to over the Nth ablation to determine the shape of tissue removed with the ablation, for example with 100 pulses.

FIG. 10C shows fitting of basis profiles from the ablation rings and discs as in FIGS. 10A, 10B and 10C to determine a linear combination of basis profiles. The basis profile B1 is determined from the first ablation ring from the first circular scan with a center of each pulse along a first circle. The basis profile B2 is determined from the second ablation ring from the second circular scan with the center of each pulse along the second circle. The basis profile Bn is determined from the Nth ablation from the Nth circular scan with the center of each pulse along the second circle. The Epithelial Ablation profile comprises a target epithelial ablation profile, for example a desired shape as described above. The target epithelial ablation profile may comprise a clearance zone, for example with a removal zone with a dimension RZ extending across the removal zone. The dimension AS extending across the entire ablation can correspond to the total ablation size. A transition zone can extend from the outer boundary of the clearance zone to the outer boundary of the ablation zone.

The basis data are fit to the epithelial ablation profile to determine a liner combination of the basis data. To optimize the ablation pulse sequence, the ablation pulse sequence can be determined with fitting of the clearance region without fitting of the transition zone, which may comprise many shapes resulting from the fitting of the pulse sequence to the clearance region with the pulse instruction vector. In some embodiments, the transition zone may also be fit to determine the linear combination, for example as described above. The liner combination of basis data comprises weights. A weight W1 comprises first weight of the linear combination. First weight W1 can be used to determine the number of pulses used with the first scan circle. For example with a first weight of 0.23, 23 pulses may be used along the first circle. A second weight W2 comprises second weight of the linear combination. Second weight W2 can be used to determine the number of pulses used with the second scan circle. For example with a second weight of 0.47, 47 pulses may be used along the second circle. An Nth weight Wn comprises an Nth weight of the linear combination. Nth weight Wn can be used to determine the number of pulses used with the Nth scan circle. For example with an Nth weight of 0.83, 83 pulses may be used along the Nth circle.

The above values are merely illustrative of the method of obtaining values, and actual values obtained in accordance with the above described method and/or system can be different.

FIGS. 11A to 11H show examples of images of epithelial fluorescence from a patient treatment. The images shown in FIGS. 11A to 11H can be sampled from a treatment, for example a treatment of 1600 pulses. To obtain the images, a UV sensitive CCD camera can be mounted on the side of the microscope beam splitter and used to image the fluorescing event of each pulse, as described above. The camera may have its own frame-capture card located in the system controller computer. A "fire laser" signal, for example TTL (5 volt) signal, can be sent to the camera to trigger frame capture with each pulse, as described above. The exposure of the image may be timed such that the entire fluorescing event will be captured. The exposure time may be limited to 100 µs to avoid capturing unwanted light, including reflections from the patient illumination and room lighting.

Figures 11A, 11B, 11C, 11D:
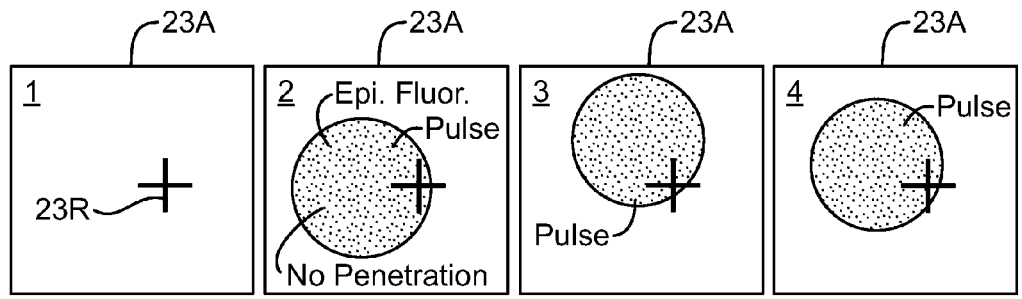
FIGS. 11A to 11H show examples of images of epithelial fluorescence, according to embodiments of the present invention.
Figures 11E, 11F, 11G, 11H:
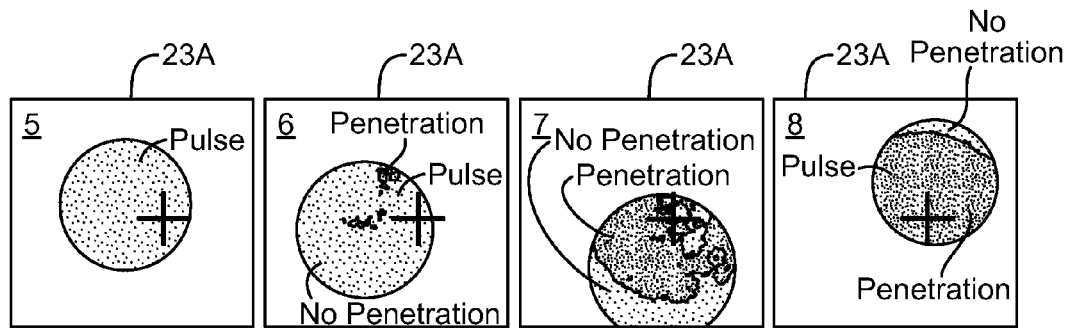

FIG. 11A shows a baseline image acquired when the laser is not fired and there is no epithelial fluorescence. FIG. 11B shows epithelial fluorescence with a first pulse at a first location, in which fluorescence extends across the first pulse location with an intensity above a threshold value. FIG. 11C shows epithelial fluorescence with a second pulse at a second location, in which fluorescence extends across the second pulse location with an intensity above the threshold value. FIG. 11D shows epithelial fluorescence with a third pulse at a third location, in which fluorescence extends across the third pulse location with an intensity above the threshold value. FIG. 11E shows epithelial fluorescence with a fourth pulse at a fourth location, in which fluorescence extends across the fourth pulse location with an intensity above the threshold value. FIG. 11F shows epithelial fluorescence with a fifth pulse at a fifth location, in which fluorescence extends across a majority of the area of the fifth pulse location with an intensity above the threshold value, and portions of the fifth pulse location comprise fluorescence intensity below the threshold value so as to indicate penetration of the epithelium. FIG. 11G shows epithelial fluorescence with a sixth pulse at a sixth location, in which fluorescence extends across a minority of the area of the sixth pulse location with an intensity above the threshold value, and portions of the sixth pulse location comprise fluorescence intensity below the threshold value so as to indicate penetration of the epithelium. FIG. 11H shows epithelial fluorescence with a seventh pulse at a seventh location, in which fluorescence extends across a minority of the area of the seventh pulse location with an intensity above the threshold value, and portions of the seventh pulse location comprise fluorescence intensity below the threshold value so as to indicate penetration of the epithelium.

The images shown in 11A to 11H comprise images sampled from a portion of the treatment, and similar images can be acquired from each pulse of the laser treatment for the entire treatment, for example with the camera triggered off the laser and coupled to the frame grabber and shown on the display as described above. The image from each pulse can be shown on the display in real time, such operator is able to visualize penetration of the epithelium with minimal interference from visible light, for example as shown in FIG. 11A which shows little interference from visible light at baseline.

Plotting General Intensity of Epithelial Fluorescence

Figure 12A:
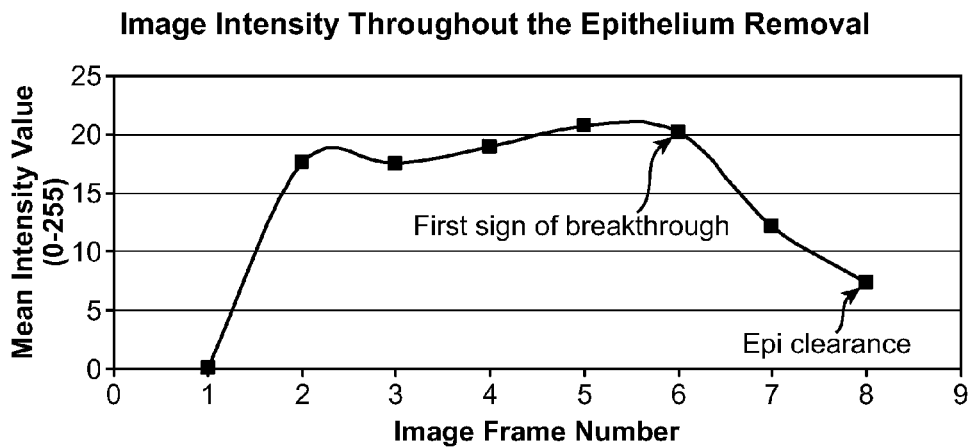
FIG. 12A shows a plot of image intensity for epithelium removal with images as in FIGS. 11A to 11H.

FIG. 12A shows a plot of image intensity for epithelium removal with images as in FIGS. 11A to 11H. This plot illustrates characteristics of the fluorescence images obtained with the above described system that can be used to detect penetration and/or clearance of the epithelium. Penetration/breakthrough of the epithelium can encompass at least some portion of the treatment area over which the epithelium which has been completely removed. Clearance of the epithelium may encompass removal of the epithelium over a majority of the surface area of the area targeted for removal. In many embodiments, penetration/breakthrough corresponds to a first amount of fluorescence and epithelial clearance corresponds to a second amount of fluorescence, the second amount smaller than the first amount.

The mean intensity value of a 20 pulse rolling average can be graphed to show intensity drop with penetration and/or epi clearance. Each laser beam pulse applied to the epithelium will fluoresce a certain threshold amount. Although the stroma may fluoresce, this amount can be substantially below the threshold amount. The amount of epithelial fluorescence can be quantified by summing the brightness value of each image for an empirical number of patients, for example 20 patients. As each pulse is applied, a specific image intensity can be expected because the exact area of epithelium irradiated is known based on the programmed size of the laser beam. By plotting the fluorescence values for each pulse, for example expected fluorescence minus measured, on a simple line graph inflexion points can signify breakthrough/penetration and clearance areas where epithelium has been removed. A running average of fluorescence values for a plurality of pulses may be used to determine penetration and/or clearance of the epithelium, for example a running average of 20 pulses. Therefore, a signal indicated epithelial penetration and/or clearance can be generated in response to at least one the laser beam size, a mean expected fluorescence value or running average of fluorescence. The signal may comprise a first signal to indicate penetration of the epithelium and a second signal to indicate clearance of the epithelium.

The physician can select among several modes of operation, for example among 1) Automated detection of penetration and/or clearance with manual stopping of the laser; 2) Automated treatment stoppage; and 3) Location specific epithelium removal.

1. Automatic Detection of Epithelial Penetration and/or Clearance.

The penetration and/or clearance of the epithelium can be detected in many ways based on the above described characteristics. In a specific example, by performing a 20-pulse rolling average on all pulses with a significant signal, for example 3.5 mm and above, an accurate inflection point can be found and fed forward to the doctor. The detection of epithelial penetration and/or clearance can be used to alert the physician and/or to stop epithelial ablation in response to epithelial penetration and/or clearance, for example based on images as described above. Because the patient's eye can move during surgery, an eye tracker can be used to monitor fluorescence automatically, and the center location of the eye can be fed from the XY trackers continuously to improve the quality of the sensor signal.

Physician Alerts

The decrease in fluorescence can trigger messages to the surgeon during treatment, for example alerting of initial breakthrough to stroma. The physician can stop the laser in response to the message, such that doctor can scrape the epithelium, for example with doctors who prefer to scrape residual epithelium. Once the doctor has scraped away residual epithelium, the doctor can continue with a refractive treatment with ablation of the stroma to correct optical errors of the eye as described above. For surgeons preferring a "no-touch" approach without scraping of the residual epithelium, the system can signal when epithelium has been penetrated and/or cleared with ablation, and the physician can select the refractive treatment with ablation of the stroma to correct optical errors of the eye.

2. Automatic Treatment Stoppage.

In some embodiments, the fluorescence signal is used control the laser and to stop laser firing automatically, for example based on the inflexion points measured as described above. In addition to triggering an alert, the system can stop at either the penetration/breakthrough amount or clearance amount, depending on what the surgeon had chosen, for example what the physician has selected prior to treatment. For example, a physician who scrapes the residual epithelium may select to stop the laser with penetration, and the physician who wishes to use a no touch procedure may select to stop the treatment with clearance of the epithelium.

3. Location Specific Ablation of Epithelium.

The real-time feedback of fluorescence imaging can control the positioning of the laser pulses. As the epithelium is cleared away, the laser can minimize, even avoid, ablation in those specific areas where epithelium has been removed.

Figure 13A:
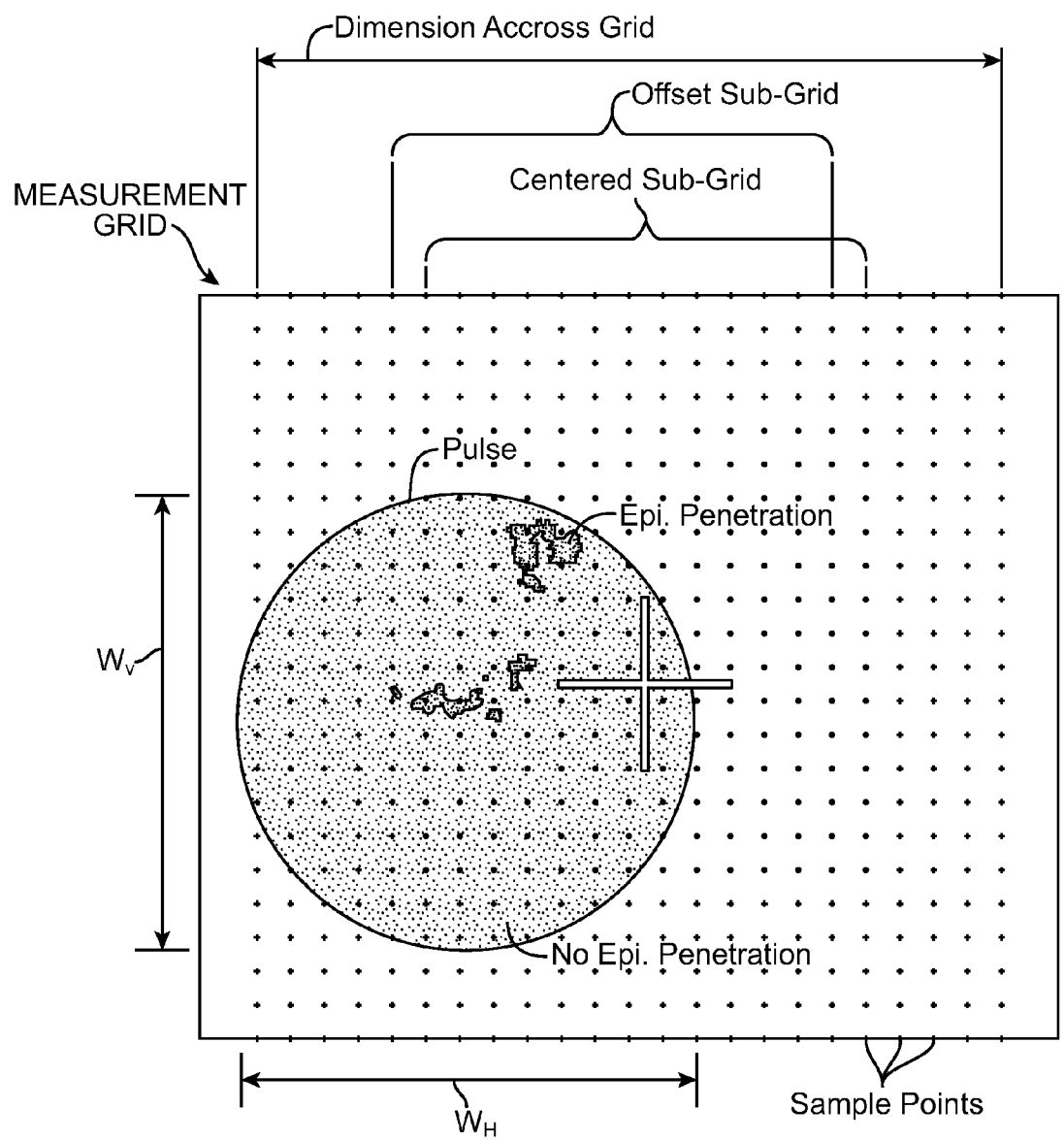
FIG. 13A shows an image of epithelial fluorescence and a grid for location specific epithelium ablation, according to embodiments of the present invention.

FIG. 13A shows an image of epithelial fluorescence and a grid for location specific epithelium ablation that can be used for location specific ablation. The image can be taken through a microscope, as described above, and the image may comprise indicia used by the physician during treatment. For example, a reticule can be used to show the physician the center of treatment. A sub-grid, for example a red grid can indicate the center of treatment. When the beam is scanned, the laser beam may not be centered on the eye, for example when a 6.5 mm beam is scanned and extends across a center of the ablation and an outer boundary of the clearance zone, as described above. A measurement grid can extend across the image, with points on the grid shown to indicate to the physician the location of the grid. There can be a color encoded sub-grid, for example a rid grid, to indicate where measurements are taken. There can be a series of images similar to FIG. 13A shown in real time, so as to show the tracking of the red grid over the center of the eye. A couple of images of showing the recognition of stromal breakthrough can be shown to the physician.

The optical imaging system can measure the fluorescence with a field of view and resolution. The image field of view and resolution may comprise many values. The image output may have resolution 640×480 pixels, although many resolutions may be used. At the distance of the camera, the field of view may be approximately 14.67×11.00 mm respectively, although the filed of view may comprise many angles.

The measurement grid can be used to sample data from the sensor array. Specific points can be measured on each image and brightness of these points continually monitored for changes in intensity, for example a change from above a threshold to below a threshold so as to indicate penetration of the epithelium. The points can be arranged in a square grid pattern, although many arrangements of points and/or lines can be used. For example the grid may comprise dimensions of 11×11 mm. The grid sample resolution may comprise about 500 micron spacing, for example 484 points total, although many grid spacing and points can be used. This grid sample area can cover an image area of the CCD camera sensor of approximately 480×480 pixels, and this amount of resolution allows one to bin pixels at the grid location to measure intensity more accurately. For example, each sample point may comprise a nine pixel bin, in which the grid sample point comprises the average intensity value of the nine-pixel square. The use of the grid can reduce the processing time of the image as only part of the data from the CCD camera sensor is used. Each image can therefore be processed in real time to generate an array of intensity values comprising 484 points, although the array many comprise many points and 484 is merely illustrative. Although reference is made to a grid, other image processing techniques such as image threshold can be used to process the fluorescence images.

Data from the laser system and/or eye tracker can be used to process the fluorescence data from the fluorescence sensor to improve the accuracy of the measurements. For example, within the above described array, data signals comprising the location of the eye, for example the central location of the eye, can be fed forward from the tracker to the processor system. The processor system can be configured to select a subset of grid values, for example from a sub-grid, which can be used for analysis of the intensity values. This smaller array may measure, for example 7×7 mm and may comprise points of the grid, for example 196 points. As the patients eye moves, the 7×7 mm array can move with the eye in response to eye position data from the eye tracker system. For example, the grid can stay centered on the eye and within the 11×11 mm grid. The sub-grid can be adjusted in response to additional parameters of the laser treatment. For example, the sub-grid can be sized and/or shaped to correspond to the laser beam size and/or shape. The sub-grid can change size and location with the beam size and location from the treatment table. For example, the grid may comprise a circular grid sized to match the diameter of a circular pulsed laser beam. The sub-grid can be moved with the laser beam as the beam scans over the tissue in response to the treatment table and eye tracker, such that the grid is placed over the position of the beam and sized with the beam. For example, the laser beam may comprise a vertical height Wv and a horizontal width Wh, and the sub-grid can be moved and sized with the beam height Wv and beam width Wh. As the position of the beam is under control of the processor, the position of the beam when the laser fires can be used to place the sub-grid over the beam in response to the position of the beam deflection component. In some embodiments, the movable beam scan component may comprise a sensor that measures position of the scan component, for example a galvanometer position sensor, such that sub-grid can be positioned on the beam in response to the measured position of the scan component.

The sub-grid can be sized to cover the optical zone. The optical zone can comprise the portion of the ablation to correct an optical defect of the eye, for example myopia, and can be bounded by a transition zone. With an 7 mm optical zone the sub-grid may have a size of at least 7 mm. With an 8 mm optical zone treatment the sub-grid may extend at least 8 mm across the fluorescence image. Values within the larger array but not within the sub-grid can be discarded.

Although reference is made to a sub-grid, many data sampling windows can be sampled from a part the fluorescence image in response to at least one of the position of the eye, the size of the laser beam, the shape of the laser beam, or a measured position of the beam scan component. For example, a spatial data sampling window can be used that corresponds to a part of the image and the part of the image selected for analysis in response to the position of the eye, the size of the laser beam, the shape of the laser beam and a measured position of the beam scan component.

The fluorescence data can be used to control the laser.

Real time intensity measurement of the fluorescence from the grid can be used to direct the laser beam. For example, 196 points can yield 196 individual intensity profiles similar to the one found in FIG. 12A. Adjacent points of high intensity above a threshold can indicate a portion of the treatment area comprising remaining epithelium. Specific tables can be used to remove tissue in localized areas in response to the number of adjacent points. The specific tables can be calculated prior to treatment such that a table can be selected in response to at least one of the area, location or shape of the fluorescence above the threshold. For example a table can be selected in response to an area of coverage of the beam with the table and the area, the location and shape of the fluorescence above the threshold. The small set of tables may reside permanently on the laser and may be used only for epithelial ablation. The tables can remove epithelium in many ways, for example varying degrees ablation over a circular area. As a safety mitigation, there can be limits to the amount of (depth) deviation allowed from a flat-bottomed ablation.

Figure 13B:
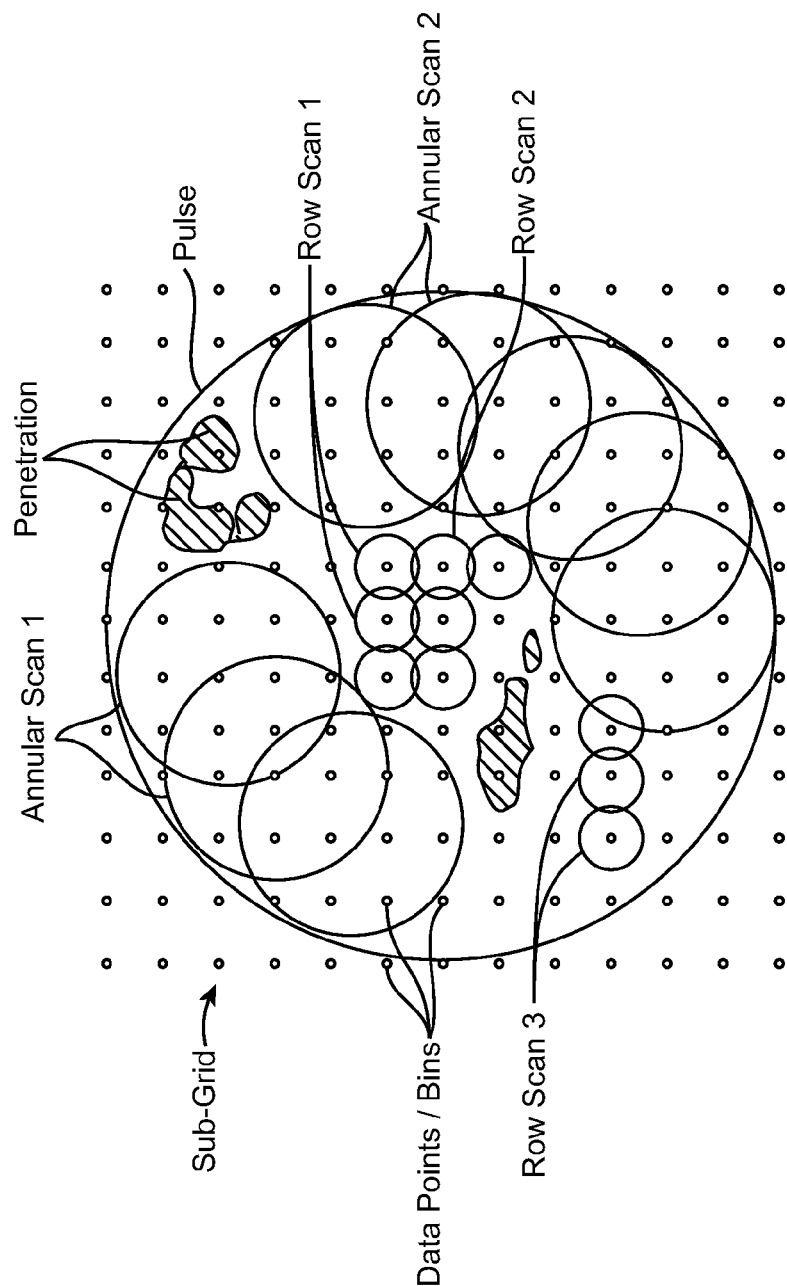
FIG. 13B shows scanning with tables in response to the measured fluorescence as in FIG. 13A.

FIG. 13B shows scanning with tables in response to the measured fluorescence as in FIG. 13A. The sub-grid can be analyzed to determine portions of the grid that are above threshold and portions below threshold so as to indicate the presence and penetration of the epithelium, respectively. A first table corresponding to an annular scan along a first portion above threshold can be selected, for example an annular scan from about 9 o'clock to 12 o'clock can be selected. A second table can be selected corresponding to a second annular scan along an arc, for example from about 2 o'clock to about 6'oclock. A third table corresponding to a first row scan can be selected. A fourth table corresponding to a second row scan can be selected. A fifth table corresponding to a fifth scan can be selected. The treatment tables can be stored in memory of the processor with coordinate references and beam sizes as described above.

Figure 14A:
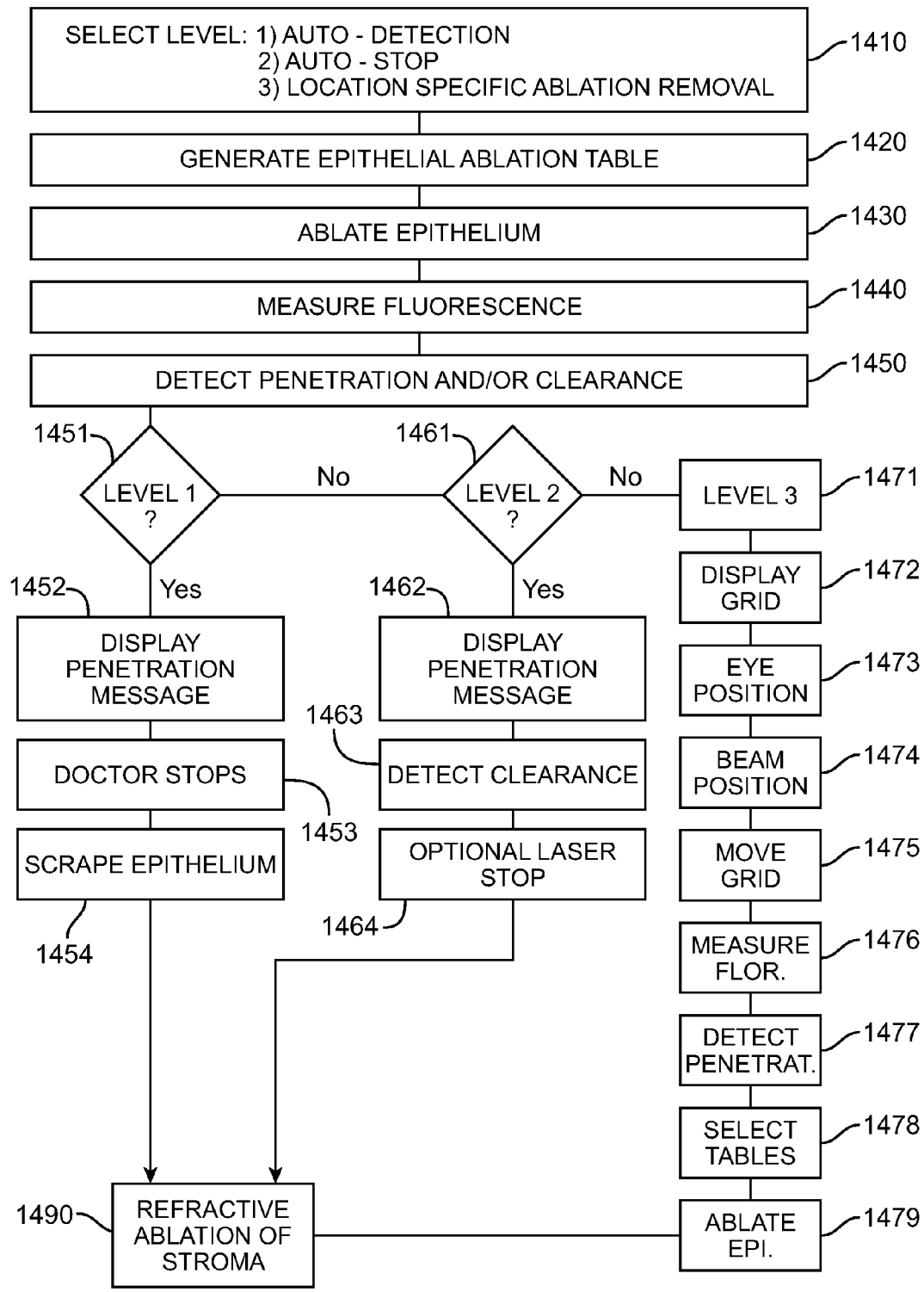
FIG. 14A shows a method of location specific epithelium ablation.

FIG. 14A shows a method 1400 of location specific epithelium ablation. Method 1400 can be implemented with a processor system, for example a processor comprising a tangible medium configured to perform method 1400. A step 1410 selects a treatment level, or operation mode. The levels can comprise: 1) an auto-detection level, 2) an auto-stop level; and 3) location specification ablation of epithelium. A step 1420 generates an epithelium ablation table, for example as described above. The table may comprise a sequence of pulses of the beam that is arranged to enhance optical feedback based on the tissue fluorescence so that areas of the epithelium larger than the beam can be ablated and tissue penetration detected, as described above. A step 1430 ablates the epithelium with the table. A step 1440 measures fluorescence, and this can be done in many ways as described above. A step 1450 detects penetration and/or clearance of the epithelium.

A step 1451 can determine that level 1 has been selected. A step 1452 displays an epithelial penetration message to the operator and/or doctor. The epithelium penetration message can be displayed in response to the fluorescence signal below a first threshold, as described above. A step 1453 stops the treatment, for example with a doctor removing a foot petal. A second message indicating epithelial clearance can also be displayed for the physician to stop the treatment when the epithelium is cleared with the laser ablation. A step 1490 ablates the stroma and/or Bowman's with a refractive correction.

A step 1461 can determine that level 2 has been selected. A step 1462 can display an epithelium penetration message. A step 1463 detects clearance of the epithelium with ablation subsequent to penetration. A step 1464 may stop the laser, for example to allow the physician to examine the exposed surface to ensure the epithelium has been removed. A step 1490 ablates the stroma and/or Bowman's with the refractive correction, for example in response to a physician depressing a foot petal after the laser has stopped.

A step 1471 can determine that level 3 has been selected. A step 1472 displays the grid, for example as described above. A step 1473 determines a position of the eye, for example with an eye tracker as described above. A step 1474 determines the laser beam position, for example as described above with reference to a beam scan component. A step 1475 moves the grid. The grid can be moved in response to at least one of the eye position, the beam position or the size of the beam. A step 1476 measures fluorescence, for example with an array comprising a grid as described above. A step 1477 detects penetration of the epithelium, for example penetration for at least one measurement point. A step 1478 selects tables to ablate remaining epithelium, for example tables as described above. A step 1479 ablates the epithelium with the selected tables. The above steps can be repeated until the epithelium is cleared. A step 1490 ablates the stroma and/or Bowman's with a refractive correction.

What is claimed is:

1. A system to ablate an eye to remove an epithelial layer disposed over a stromal layer in a cornea of the eye, the system comprising:
   a laser to generate a pulsed beam of an ablative radiation;
   a movable structure disposed along the laser beam path to adjust a size of the laser beam to at least one smaller size and at least one larger size;
   a movable scan component configured to scan the adjustably sized laser beam over a region of the eye in accordance with a pulse sequence to ablate the epithelial layer; and
   a processor system comprising a tangible medium and a memory, the processor system coupled to the laser, the movable structure and the movable scan component, the processor system configured to scan the ablative radiation to vary a location of the beam in accordance with the pulse sequence, wherein the pulse sequence is arranged in response to a plurality of epithelial layer ring shaped basis profiles, wherein at least some of the plurality of epithelial layer ring shaped basis profiles each comprise a central portion corresponding to no ablation wherein the pulsed beam of the ablative radiation removes the epithelial layer to expose at least one of the stromal layer or bowman's membrane and wherein the sequence of pulses of the beam is arranged to enhance optical feedback based on the tissue fluorescence so that areas of the epithelium larger than the beam can be ablated and tissue penetration detected.

2. The system of claim 1 wherein the processor system is configured to scan the ablative radiation in response to a linear combination of the plurality of ring shaped basis profiles.

3. The system of claim 1 wherein the processor system is configured to determine a first of the plurality of ring shaped basis profiles from a first pulse size scanned along a first circle and wherein the processor system is configured to determine a second of the plurality of ring shaped basis profiles is determined from a second pulse size scanned along a second circle.

4. The system of claim 3 wherein the processor system is configured to size the first circle and the second circle to align an outer boundary of the first ring shaped basis profile with an outer boundary of the second ring shaped basis profile.

5. The system of claim 4 wherein the processor system is configured to size the first pulse size and the second pulse size to align the outer boundary of the first ring shaped basis profile with the outer boundary of the second ring shaped basis profile.

6. The system of claim 1 wherein processor system is configured to arrange the pulse sequence in response to at least one epithelial layer disc shaped basis profile in combination with the plurality of ring shaped basis profiles.

7. The system of claim 6 wherein the processor system is configured to store the plurality of ring shaped basis profiles and each comprises a central portion corresponding to no ablation and wherein the processor system is configured to store the at least one disc shaped basis profile and the disc shaped basis profile comprises a central portion corresponding to a maximum depth of ablation of the at least one disc shape basis profile.

* * * * *